United States Patent [19]
Chien et al.

[11] Patent Number: 5,788,983
[45] Date of Patent: *Aug. 4, 1998

[54] TRANSDERMAL CONTROLLED DELIVERY OF PHARMACEUTICALS AT VARIABLE DOSAGE RATES AND PROCESSES

[75] Inventors: Yie W. Chien, North Brunswick, N.J.; Guo-Shen Chen, Zheijiung, China; Te-Yen Chien, Branchburg, N.J.

[73] Assignee: Rutgers, The State University of New Jersey, New Brunswick, N.J.

[*] Notice: The portion of the term of this patent subsequent to Jun. 11, 2009, has been disclaimed.

[21] Appl. No.: 943,169

[22] Filed: Sep. 14, 1992

Related U.S. Application Data

[63] Continuation-in-part of Ser. No. 332,471, Apr. 3, 1989, abandoned.
[51] Int. Cl.⁶ ............................................ A61F 13/02
[52] U.S. Cl. .................................... 424/449; 424/448
[58] Field of Search .............................. 424/449, 448

[56] References Cited

U.S. PATENT DOCUMENTS

| | | | |
|---|---|---|---|
| 3,419,578 | 12/1968 | Fitzmaurice et al. | 260/345 |
| 3,598,122 | 8/1971 | Zaffaroni | 128/268 |
| 4,379,454 | 4/1983 | Campbell et al. | 604/897 |
| 4,624,665 | 11/1986 | Nuwayser | 604/307 |
| 4,640,689 | 2/1987 | Sibalis | 604/20 |
| 4,666,441 | 5/1987 | Andriola et al. | 604/897 |
| 4,687,481 | 8/1987 | Nuwayser | 604/897 |
| 4,708,746 | 11/1987 | Sibalis | 604/20 |
| 4,743,249 | 5/1988 | Loveland | 424/449 |
| 4,788,062 | 11/1988 | Gale et al. | 424/449 |
| 4,816,258 | 3/1989 | Nepberge et al. | 426/448 |
| 4,818,540 | 4/1989 | Chien et al. | 424/448 |
| 4,911,707 | 3/1990 | Heiber et al. | 424/449 |
| 4,913,905 | 4/1990 | Frankhauser et al. | 424/449 |
| 4,917,688 | 4/1990 | Nelson et al. | 604/306 |
| 4,931,281 | 6/1990 | Kim et al. | 424/448 |
| 4,959,365 | 9/1990 | Francoeur et al. | 514/237.5 |
| 4,994,049 | 2/1991 | Latzke et al. | 604/307 |
| 5,016,652 | 5/1991 | Rose et al. | 131/270 |
| 5,023,084 | 6/1991 | Chien et al. | 424/448 |
| 5,051,259 | 9/1991 | Olsen et. al. | 424/443 |
| 5,064,422 | 11/1991 | Wick | 604/307 |
| 5,066,494 | 11/1991 | Becher | 424/448 |
| 5,071,656 | 12/1991 | Lee et al. | 424/448 |
| 5,128,124 | 7/1992 | Frankhauser et al. | 424/449 |
| 5,190,962 | 3/1993 | Barberich et al. | 514/356 |
| 5,317,009 | 5/1994 | Lee-Huang et al. | 514/8 |

FOREIGN PATENT DOCUMENTS

| | | |
|---|---|---|
| 0 259 136 | 9/1987 | European Pat. Off. . |
| 0 259 136 A2 | 3/1988 | European Pat. Off. . |
| 0 285 563 | 3/1988 | European Pat. Off. . |
| 2161073 | 1/1986 | United Kingdom . |

OTHER PUBLICATIONS

"Estrogen Replacement Therapy by Transdermal Estradiol Administration" Am. J. Obstet Gynecol, Jul., 1983, vol. 146, No. 5 (533) Laufer et al.

"Transdermal Dual–Controlled Delivery of Contraceptive Drugs: Formulation Development, in vitro and in vivo Evaluations, and Clinical Performance," Yie. W. Chien, et. al, Pharmaceutical Research, vol. 6, No. 12, 1989.

*Primary Examiner*—Jyothsan Venkat
*Attorney, Agent, or Firm*—Schwegman, Lundberg, Woessner & Kluth, P.A.

[57] ABSTRACT

Transdermal polymer dosage units are provided which comprise a backing layer and a reservoir layer. The reservoir layer can have multiple regions which contact the skin during use, optionally may have different pharmaceuticals, may provide variable rate of transdermal absorption, and may provide the pharmaceuticals in the form of microreservoirs or one or more macroreservoirs. The reservoir region can comprise a macroreservoir of one or more pharmaceuticals wherein the reservoir is bounded by a backing layer and a layer of a substantially non-porous permeability-regulating polymer membrane which directly or indirectly contacts the skin during transdermal administration. Also, provided is a process of transdermal administration of pharmaceuticals using the novel dosage units.

11 Claims, 18 Drawing Sheets

5,788,983

TRANSDERMAL CONTROLLED DELIVERY OF PHARMACEUTICALS AT VARIABLE DOSAGE RATES AND PROCESSES

CROSS-REFERENCE TO RELATED APPLICATION

This application is a continuation-in-part of U.S. application Ser. No. 07/332,471, filed Apr. 3, 1989 now abandoned.

TECHNICAL FIELD

A novel transdermal absorption dosage unit by which multiple pharmaceuticals can be provided for transdermal absorption simultaneously at different or variable dosage rates and at relatively constant permeation profiles. The dosage units can provide the desired differences or variation in the dosage rates by providing multiregional areas of the dosage unit which have different compositions with respect to the pharmaceuticals. The novel dosage units of this invention can also provide controlled and variable dosage rates of two or more pharmaceuticals on a simultaneous basis from a single reservoir area. A single dosage area can comprise a reservoir in which the pharmaceuticals are in liquid state and are contained by a permeability-regulating membrane, which can come in contact either directly or indirectly with the skin of the subject being treated. The pharmaceuticals administered by the dosage unit of this invention can vary widely. Additionally, this invention relates to an improved process for transdermal systemic delivery of pharmaceuticals.

BACKGROUND ART

It has been found that certain pharmaceuticals are absorbed to a degree through the skin. This is referred to as transdermal absorption. One means of transdermal absorption has been to disperse the pharmaceutical within a polymeric disc or a container of a gel and then contacting an area of the skin of the subject to be treated with the disc or gel containing the pharmaceutical. Problems encountered in the past include adequate control over the rate and duration of transdermal absorption or the rate can be too slow in the case of certain dosage forms, especially from pharmaceutical-containing discs or pharmaceutical-containing gel container dosage units. It has been found that the transdermal absorption rates of certain pharmaceuticals can be increased by coadministering one or more transdermal absorption-enhancing agents with the pharmaceutical to be absorbed when compounding the polymeric disc or the pharmaceutical-containing gel.

It is desired to improve the dosage unit forms or devices by which pharmaceuticals are transdermally absorbed, especially in view of the importance of administering pharmaceuticals by this means. Desired transdermal absorption of pharmaceuticals would provide an avoidance of gastrointestinal incompatibility with the pharmaceuticals and unwanted destruction of the pharmaceuticals by metabolism in the gastrointestinal tract and by a hepatic "first-pass" metabolism. The transdermal absorption minimizes inter- and intra-patient variations regarding such incompatibilities and metabolisms. By transdermal absorption, it is deemed possible to provide a more constant pharmaceutical concentration in the body and to realize a greater pharmacological efficacy. It is possible, by proper transdermal absorption, to reduce the frequency of dosing. Transdermal administration provides most of the advantages of intravenous dosing without the necessity of hospitalization and the accompanying discomfort and inconvenience.

It is desired to improve the administration by transdermal means of pharmaceuticals by modulating the delivery of pharmaceuticals, desirably at substantially constant rates. It is also desired to administer two or more pharmaceuticals with synergistic therapeutic activities, simultaneously, especially at variable dosage rates. For example, it is often desired in regulating fertility by administering simultaneously an estrogenic steroid, such as 17-beta-estradiol (commonly referred to as "estradiol"), and also to administer simultaneously a progestational steroid. These hormonal steroids normally have differing absorption rates and require different dosage amounts of the respective steroids. These steroids are used for either fertility regulation or for the treatment of postmenopausal syndrome and other hormonal replacement therapy.

It is desired to provide such improved dosage units which enable controlled delivery of pharmaceuticals, including steroidal hormones, with the possibility of two or more pharmaceuticals being administered simultaneously at controlled and variable dosage rates. Furthermore, it is desired to provide improved methods of administration of pharmaceuticals, including the simultaneous administration of multiple pharmaceuticals with different pharmacological activities, including hormonal activities, to achieve a synergistic effect.

SUMMARY OF INVENTION

This invention relates to a transdermal dosage unit for administration of one or more pharmaceuticals simultaneously at controlled and variable rates of transdermal delivery. The transdermal dosage unit provided by this invention comprises the following:

a) a backing layer which is impervious to the ingredients of the dosage unit;

b) a reservoir having present for transdermal absorption one or more pharmaceuticals, said multiple pharmaceuticals being compatible and being delivered simultaneously, preferably at constant rates of administration, over a predetermined duration of administration;

c) means which desirably provide variable transdermal absorption rates of the one or multiple pharmaceuticals in an effective amount to result in substantially constant systemic levels continuously for at least 24 hours; and d) an adhesive means to affix said dosage unit to the intact skin of a subject receiving the therapy provided thereby.

The reservoir can be provided in multiregions, which are in contact with the skin of the subject undergoing treatment with said dosage unit, at least two of which provide transdermal absorption of one or more pharmaceuticals simultaneously from each of the regions.

The dosage unit permits two or more pharmaceuticals to be administered transdermally and simultaneously through the intact skin to achieve therapeutically effective systemic concentrations and to maintain the therapeutic concentrations at substantially constant levels continuously for at least a 24-hour period. Pharmaceuticals which are subject to hepatic "first-pass" elimination or which are irritating to the gastrointestinal tract and which have synergistic or additive effect when used in combination can be selected for administration by the dosage units of this invention. One of the combinations of pharmaceuticals which can be administered by the dosage units of this invention is a combination of progestational and estrogenic steroids, natural or synthetic, for the regulation of fertility or treatment of postmenopausal syndrome or other hormonal steroid therapy. Other possible combinations of pharmaceuticals which can be administered by the dosage units include: (1) testosterone and 17-methyl testosterone, (2) testosterone and estradiol, (3) AZT and DDC (or DDI), (4) a proprandol and hydrochlothrazide, (5) bumetamide and cyclothiazide. The reservoir can comprise mono- or multi-regional reservoir compartments which are adapted to provide controlled and variable delivery of two or more pharmaceuticals on a simultaneous basis and at rates which are substantially constant continuously for a period of at least 24 hours or longer. The mono- or multi-regional pharmaceutical reservoir compartment or compartments can be provided by forming the reservoir between two sheets of pharmaceutical-impermeable protective plastic laminates: the one laminate layer comprising a peelable release liner to be removed just before application of the dosage unit to the subject of the therapy and another layer being a backing layer to house and to protect the pharmaceutical reservoir compartments from the environment as well as to control and to restrict the pharmaceuticals to be delivered transdermally to the skin of the subject being treated.

The rate of transdermal delivery can be achieved by controlling the solubility of the respective pharmaceutical or pharmaceuticals and the permeability across a permeability-regulating membrane and the skin. The rates of transdermal permeation can be programmed at therapeutically-effective ratios. The solubility of the one or more pharmaceuticals administered from said dosage unit as stated above can be provided from a single reservoir area or from multiple reservoir areas of the transdermal dosage unit provided hereby by changing, regulating or varying the rate of transdermal permeation.

In providing the preferred dosage units of this invention, it is useful and necessary to study the differences in solubility and permeability of the one or more pharmaceuticals to be coadministered by the application of the dosage units of this invention, whether they are mono- or multi-regional drug reservoir compartment dosage units whereby the one or more pharmaceuticals can be delivered transdermally at variable dosage rates to achieve desired therapeutically-effective ratio or ratios.

If a multiregional reservoir is used, it is desirable that at least one region has at least one pharmaceutical present in the form of a macroreservoir or microreservoirs.

If a macroreservoir form is used, it is desired that the macroreservoir be covered by application to the pharmaceutical-releasing surface of the reservoir a permeability-regulating polymeric membrane, which is non-porous. If microreservoirs are used, the preferred non-porous permeability-regulating membrane is a (ethylene/vinyl acetate) copolymer wherein the vinyl acetate content can be in the range (by mean weight) of about 4.6 percent to about 50 percent; presently preferred in the mean weight range from about 18 to about 40 percent.

It is also presently preferred that the rate of one or more of the pharmaceuticals provided by the dosage unit can be made variable, for example, by using a combination of mutually miscible, bioacceptable solvents. It has been found suitable to use, for example, certain mutually miscible, bioacceptable water-organic solvent combinations, such as certain water-ethyl alcohol combinations. It has been found preferable, for example, in simultaneous transdermal systemic delivery of an estrogen, such as estradiol, and a progestin, such as levonorgestrel, to use a water-ethyl alcohol combination wherein the content (by volume) of ethyl alcohol is about 40 to about 85 percent based on the combined volume of water and ethyl alcohol.

If at least one pharmaceutical is to be present in the reservoir in the form of microreservoirs of the pharmaceutical, the pharmaceutical can be dissolved in a biocompatible liquid which can provide variability of the transdermal absorption rate if desired. For example, combinations of water and polyethylene glycol or the like can be used. The pharmaceutical can be dispersed and dissolved in liquid before dispersion into a biocompatible polymeric material, such as an adhesive polymer, elastomeric polymer or gelling polymer and then stirred at sufficiently high speed to form a pharmaceutical-containing polymeric material wherein microreservoirs of the dissolved pharmaceutical are dispersed in a polymeric material. The polymer selected must be biocompatible, compatible with the pharmaceuticals microdispersed therein and permit the release of the pharmaceuticals for the desired transdermal absorption.

Provided hereby also is a novel method of transdermal absorption of pharmaceuticals using the transdermal dosage units of this invention.

BRIEF DESCRIPTION OF THE DRAWINGS

FIG. 2-(A) represents a top view of the dosage unit of FIG. 2 shown in cross-sectional view.

DETAILED DESCRIPTION OF THE INVENTION AND THE PREFERRED EMBODIMENTS

The backing layer can be made of any suitable material which is impermeable to the pharmaceuticals dispersed within the adjacent reservoir layer. The backing layer serves as a protective cover and provides also a support function. The backing can be formed so that it is essentially the same size layer as the central reservoir containing one or more pharmaceuticals or it can be of larger dimension so that it can extend beyond the side of the central reservoir or over-lay the side or sides of the reservoir and then can extend outwardly in a manner that the surface of the extension of the backing layer can be a base for a pressure-sensitive adhesive ring to hold the dosage unit in intimate contact with the skin of the subject treated.

Examples of materials suitable for making the backing layer are films of high and low density polyethylene, polypropylene, polyvinylchloride, polyesters such as poly (ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the pharmaceutical-containing reservoir. The backing layer can be any appropriate thickness which will provide the desired protective and support functions. A suitable thickness will be from about 10 to about 200 microns. Desirably, the thickness will be from about 15 to about 150 microns, and preferably be from about 20 to about 100 microns.

Figure 1:
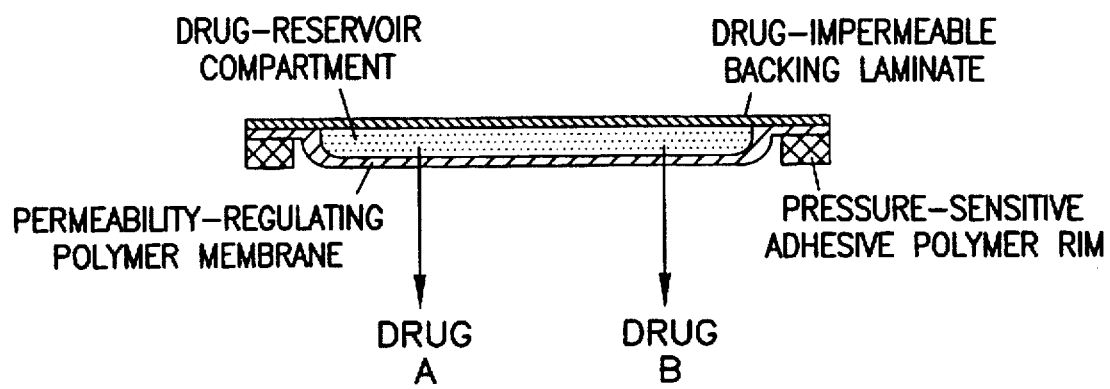
FIG. 1 shows a dosage unit of this invention, wherein the reservoir for the pharmaceuticals contains two pharmaceuticals, A and B, in a macroreservoir form. The macroreservoir is covered by a pharmaceutical permeability-regulating polymer membrane. The dosage unit is shown as a cross-sectional view. The dosage unit has a pressure sensitive adhesive polymeric ring in a peripheral location with respect to the macroreservoir containing pharmaceuticals A and B. Shown as FIG. 1-(A) is a top view of the dosage unit of FIG. 1.
Figure 1A:
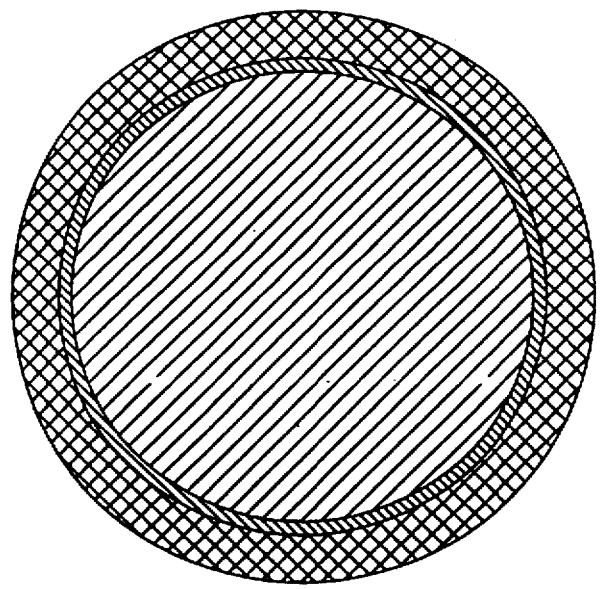

In illustration of the dosage units provided by this invention, the FIG. 1 dosage unit is provided. The backing layer is selected from the above illustrative backing layer pharmaceutical-impermeable laminates. It has been found suitable to use as backing layer consisting of a laminate of aluminum foil and polyester film which is heat sealable, such as sold by 3M as Scotch Pak 1009. A non-porous membrane such as a non-porous (ethylene/vinyl acetate) copolymer film, which is bioacceptable, can be used as the permeability-regulating membrane. The non-porous (ethylene/vinyl acetate) copolymer film can be precast on a siliconized paper or other substrates to provide a receptacle of suitable dimensions to form the walls of the reservoir. To this reservoir receptacle is added the desired form of one or more pharmaceuticals. The pharmaceuticals can be dissolved in a solution for the pharmaceuticals and added in a suitable amount to the reservoir receptacle. Then, a sheet of the backing layer is selected. It is placed over the reservoir receptacle and heat sealed thereto. It has been found that a sealing temperature of about 350°–400° F., such as 370° F., can ordinarily be used and a sealing pressure of 50 psi is suitable. The sealing conditions can be varied widely depending upon the thermal characters of the backing layer and permeability-regulating membrane used. The backing layer can extend around the sides of the reservoir receptacle. On a siliconized release liner using a pattern to form a peripheral adhesive ring, a peripheral ring of adhesive polymer is formed. This adhesive polymer ring mounted on the siliconized release liner is mounted and sealed to the outwardly extending portion of the backing layer.

The adhesive polymer used in forming the ring can have a pharmaceutical microdispersed therein, for example, by dissolving the pharmaceutical in a biocompatible solution and then stirring at a sufficiently high intensity to cause the pharmaceutical to be microdispersed in the adhesive polymer to form microreservoirs.

The one or more pharmaceuticals present in the reservoirs can be selected from a wide variety. If desired, a gelling agent can be added to the macroreservoir solution to provide the macroreservoir in a semi-solid state. Also, the macroreservoir solution can be also microdispersed within an adhesive polymer as described above in connection with formation of the peripheral ring of the FIG. 1 dosage unit. This results in the pharmaceutical component of the reservoir to be provided as microreservoirs of the pharmaceutical.

The dosage units provided thereby can be stored appropriately until it is desired to treat a subject with the dosage unit whereupon after removal of the peelable release liner, it is applied to the skin of the subject.

FIG. 1-(A) shows the top view of the dosage unit of FIG. 1.

Figure 2:
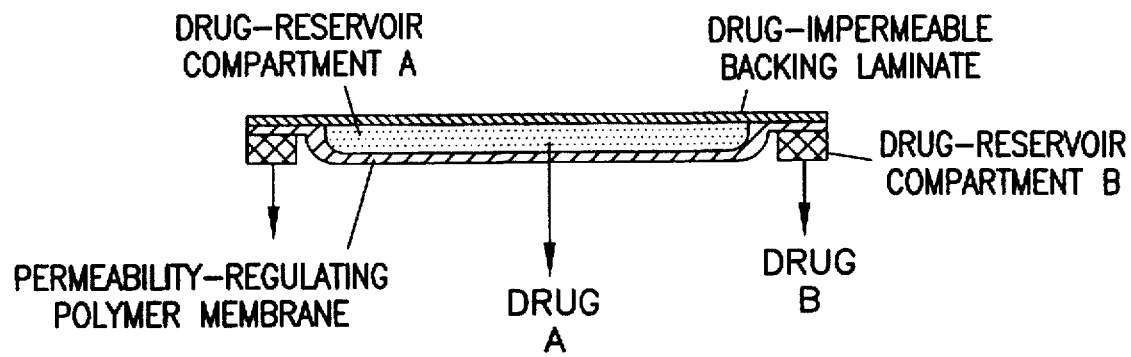
FIG. 2 shows a dosage unit of this invention similar to that shown in FIG. 1 and FIG. 1-(A) with the exception that the peripheral ring is made of a polymeric adhesive material and comprises a microreservoir containing pharmaceutical B. The central compartment A consists of a macroreservoir containing pharmaceutical A.
Figure 2A:
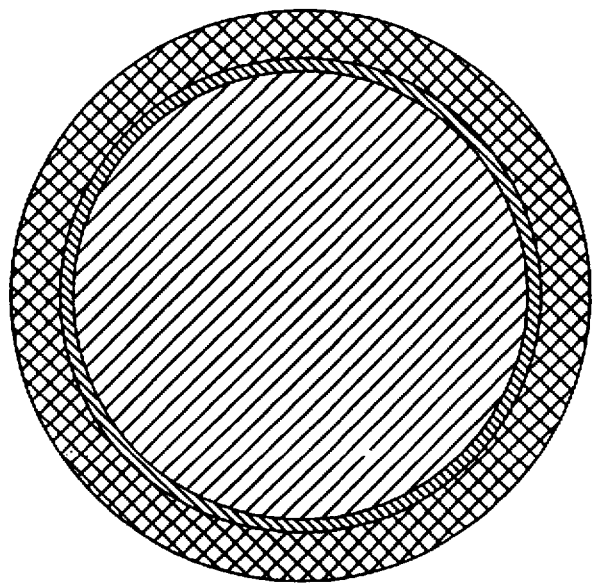

FIG. 2 is substantially the same dosage unit design as provided by FIG. 1 with the exception that the pharmaceutical A is contained in the macroreservoir compartment (drug-reservoir compartment A) and pharmaceutical B is present in microreservoir form in the peripheral adhesive ring (drug-reservoir compartment B). Provided is FIG. 2(A) showing the top view of the dosage unit of FIG. 2.

The permeability-regulating polymer membrane as employed in the dosage units shown in FIG. 1 and FIG. 2 can be selected from a number of polymeric membranes depending upon the rate of delivery desired and the pharmaceuticals administered by the dosage unit.

The permeability-regulating polymer membranes used are "non-porous", meaning essentially free of pores. The permeability-regulating polymer membrane permits the pharmaceutical to pass through the membrane along with any skin permeation-enhancing agent used. It has been found that a suitable non-porous polymer film for use in making the permeability-regulating membrane for dosage units having a number of pharmaceutical components is a (ethylene/vinyl acetate) copolymer film. The vinyl acetate content of the film is suitably from about 4.5 to about 50 percent by mean weight of the copolymer, presently preferred for many uses the content is in the range of about 18 to about 40 percent by mean weight. The thickness of the film can also vary. Generally speaking, the thicker the film used, the slower the rate of transdermal absorption of the pharmaceutical component present in the reservoir. It has been found that ordinarily a membrane can be selected from those having a thickness of about 10 to about 100 microns. Ordinarily, a membrane having a thickness of about 20 to about 80 microns permits desired transdermal absorption and adequate strength. Other polymeric films can also be used so long as they are non-porous, bioacceptable, permit the pharmaceutical component to be transdermally absorbed at a desired rate and have adequate dimensional strength.

The reservoir medium employed to dissolve the pharmaceutical component in either a macroreservoir or microreservoirs can vary widely. It is desired that the reservoir medium can be prepared from a combination of two miscible co-solvents. It has been found that certain combinations of ethanol and water work well to provide high rates of transdermal absorption, which are constant, and give variability in the absorption rates. For example, if the pharmaceutical component has one or two hormonal steroids, for example, estradiol and a progestin, such as levonorgestrel, certain combinations of ethanol and water can be used as the reservoir medium to provide desirable constant rates of transdermal absorption over a period of 24 hours or longer and variability in the rates of absorption. It has been found that the combination of ethanol and water having about 55 to 85 percent ethanol content, preferably about 60 to about 80 percent, and more preferably about 70 percent ethanol provide maximal rate of transdermal absorption. Combinations of other solvents can also be used so long as they provide the desired results.

It has also been found desirable to use a $C_3$–$C_4$ alkane diol as the reservoir solvent. Preferred diol compounds useful in the compositions of the present invention include 1,2-propanediol, 1,3-propanediol, 1,2-butanediol, 1,3-butanediol, 1,4-butanediol, or mixtures of these diol compounds. In compositions of the present invention, 1,2-propanediol and 1,2-butanediol are more preferred diol compounds; 1,2-propanediol is an especially preferred diol compound.

If one of the $C_3$–$C_4$ alkane diols is selected for use as a reservoir solvent, the amount used will vary depending upon the pharmaceutical component and other agents present. Ordinarily, an amount of at least about 20 percent by weight of the solvent is used. Preferably, in making many dosage units, an amount of about 30 to about 90 percent is suitable, if, for example, 1,2-propanediol is used.

It is also desirable to use in combination with the miscible co-solvents by incorporating other agents, such as transdermal absorption-enhancing agents. It has been found suitable to use in combination with the combination of ethanol and water, an amount of a long chain alkanoic acid, such as oleic acid, or long-chain alcohol having, for example, decyl or lauryl alcohol. It has been also found useful to have present an effective amount of a lower alkyl ester of lactic acid such as ethyl lactate. Also, it has been found useful to have present an amount of agents sold under the designation Ceraphil, for example, Ceraphil 31 which has lauryl and myristyl lactate ester and lauryl and myristyl alcohol components.

A suitable reservoir solution has been found to have the following weight ratio: Ceraphil 31, n-decyl alcohol, ethyl lactate and propylene alcohol, 1:1:1:2.

If two pharmaceuticals are present in a reservoir, either of the macroreservoir or microreservoir type, at least one of the pharmaceuticals should be present in less than saturated amount in order that the absorption rate ratios of the two pharmaceuticals can be varied and also be maintained at a constant rate ratio.

Aqueous gels of organic polymers which are bioacceptable and compatible with other components of a pharmaceutical-containing reservoir can be used to convert the reservoir medium to a semi-solid state. For example, a small amount of such aqueous gels as gelatin, agar, pectin, methyl cellulose and polyethylene glycols, hydroxypropyl cellulose, and polyvinyl pyrrolidone can be used. Ordinarily, a small amount of aqueous gels is adequate to provide the desired increase in viscosity or semi-solid state, for example, 1 to 4 percent in the use of pectin or agar.

If it is desired that the pharmaceutical in a reservoir is present as microreservoirs, the microreservoirs can be formed by dissolving the pharmaceutical component in a desired reservoir medium, which is not a solvent for the polymeric material desired to be used in making the microreservoirs. A number of polymers are suitable, for example, a number of adhesive polymers can be used, for example, a number of polyacrylate-based adhesive polymers, silicone elastomers, polyisobutylene, and the like.

The polymeric material selected must permit the pharmaceutical to be released for the desired transdermal absorption and not substantially affect the pharmaceutical component or the permeability-regulating membrane or other components. The reservoir medium containing dissolved/dispersed pharmaceutical and the polymeric material are combined in a suitable amount and agitated using suitable stirring or dispersing means to cause microreservoirs to be formed and homogeneously dispersed in the polymeric material. It is normally desired that the microreservoirs be of a micronic diameter, such as 2 to about 200 microns, usually preferably about 5 to about 100 microns in diameter.

The adhesive polymers used in forming the adhesive element can be selected from known adhesives which are bioacceptable and pressure-sensitive. It is suitable that the adhesive element be in the form of a ring peripheral to a central reservoir, if that is the type of dosage unit of the invention used. Known polyacrylate, polyisobutylene, silicone or the like adhesive polymers can be used. If a peripheral ring is made of such adhesive polymer, it can contain a pharmaceutical which is different from the pharmaceutical component of the central reservoir. The pharmaceutical from the peripheral ring can be present as microreservoirs or can be present in matrix polymer form wherein the pharmaceutical is microdispersed in the adhesive polymer.

The dosage units can vary in surface area as desired. Generally, they do not exceed about 100 sq cm in area, suitably about 5 to about 80 sq cm, preferably about 10 to about 40 sq cm, generally about 5 to about 50 sq cm being a more preferable size. The dosage units can vary in shape as desired, such as circular, square, rectangular or other desired shape.

The dosage units can be, as stated above, multi-regional wherein at least one pharmaceutical is present in one or more regions. The pharmaceuticals in such multi-regional dosage units of this invention are transdermally absorbed therefrom. The multi-regions can be in a form of a central core, with one or more concentric circular bands surrounding the core, in a form of adjacent rectangular regions, or other suitable arrangements of the multi-regions.

The multi-regions can have the same or different pharmaceuticals to provide transdermal absorption thereof. The multi-regions can be in the form wherein the pharmaceutical is present in a macroreservoir covered with only a permeability-regulating polymer membrane, in a form wherein the pharmaceutical is in the form of microreservoirs wherein the region is covered or not covered with a permeability-regulating membrane, or one or more of the regions are in the form of a pharmaceutical-dispersing polymer matrix disc. It is preferred that at least one region of a multi-regional dosage unit of this invention be a macroreservoir covered with a permeability-regulating polymer membrane and provide a constant rate for at least 24 hours and the rate can be varied as desired.

A wide range of pharmaceuticals can be administered by the dosage units of this invention, so long as they are capable of being administered transdermally. It has been found that the dosage units are especially useful in administering two pharmaceuticals from a reservoir covered with a permeability-regulating membrane wherein at least one pharmaceutical is contained in a reservoir medium in less than a saturated condition. Thereby, the pharmaceutical can be provided in a constant rate ratio for an extended number of hours, for example, at least a 24-hour period. Such dosage unit of this invention is especially useful in providing a combination of estrogenic and progestational steroids for either fertility regulation or estrogen replacement therapy. The reservoir medium can be modified to provide a variable rate of one or both of the steroids (or other pharmaceuticals) and the corresponding absorption rate ratios.

With regard to estrogenic steroids, 17-beta-estradiol is a natural and a preferred estrogen. Derivatives of 17-beta-estradiol which are biocompatible, capable of being absorbed transdermally and preferably bioconvertible to 17-beta-estradiol can also be used, if the amount of absorption meets the required daily dose of the estrogen component and if the steroid components are compatible. Such derivatives of estradiol can be selected from esters, either mono- or di-esters. The monoesters can be either 3- or 17-esters. The estradiol esters can be, illustratively speaking, estradiol-3, 17-diacetate; estradiol-3-acetate; estradiol-17-acetate; estradiol-3,17-divalerate; estradiol-3-valerate; estradiol-17-valerate; 3-mono, 17 mono- and 3,17-dipivilate esters; 3-mono, 17-mono and 3,17-dipropionate esters; corresponding cypionate, heptanoate, benzoate and the like esters; ethinyl estradiol; estrone; estriol; and other estrogenic steroids and derivatives thereof which are transdermally absorbable, including benzestrol, chlorotrianisene, dienestrol, mestranol, and the like.

The progestational steroids can be selected from norethindrone, norgestimate, levonorgestrel (or norgestrel containing both levonorgestrel and its (+) enantiomer), norethynodrel, dydrogesterone, ethynodiol diacetate, desogestrel, 3-keto-desogestrel, hydroxyprogesterone caproate, medroxyprogesterone acetate, norethindrone, norethindrone acetate, norgestrel, progesterone, and the like.

Steroids which are androgenic can also be used in making the dosage units of this invention such as testosterone and its esters, such as testosterone enanthate, 17-alpha-methyl testosterone, 19-nortestosterone and its esters, such as nandrolone decanoate and the like.

Transdermal delivery of testosterone and/or 17-alpha-methyl testosterone could be used in the treatment of hypogonadism or used as male contraceptive. When delivered in combination with an estrogen, such as 17-beta-estradiol, from the biregional patch, it could minimize the side effects of delivering androgen alone. These side effects include: muscular overdevelopment, weight gain, acne and increase in libido.

Transdermal delivery of medroxy progesterone acetate (MPA) can be used in the treatment of secondary amenorrhea and abnormal uterine bleeding due to hormonal inbalance. When delivered in combination with an estrogen, such as 17-beta-estradiol, from the biregional patch, it could minimize the side effects encountered by taking oral MPA (Provera, by Upjohn). These side effects include breakthrough bleeding, spotting, edema, change in menstrual flow, change in weight, acne, rash and insomnia, etc.

The ratios and the amounts of the estrogens and progestins to be administered on a daily basis are known to those skilled in the art. Reference is made, for example, to U.S. Pat. No. 5,023,084.

Other pharmaceuticals, either alone or in combination, can be selected for use in carrying out this invention and can be selected from the following: alpha-|1(methylamino)-ethyl|-benzene methanol, which is useful as an adrenergic (bronchodilator); buprenorphine, N-phenyl-N-|1-(2-phenyl-ethyl)-4-piperidinyl| propanamide, useful as a narcotic analgesic; furosemide and 6-chloro-3, 4-dihydro-2H-1,2,4-benzothiadiazine-7-sulfonamide 1,1-dioxide, useful as diuretics; and 2-diphenylmethoxy-N, N-dimethylethanamine, useful as an antihistamine. Other useful drugs include: anti-HIV drugs, such as dideoxy nucleoside; antimicrobial agents, such as penicillins, cephalosporins, tetracycline, oxytetracycline, chlortetracycline, chloramphenicol and sulfonamides; sedatives and hypnotics, such as pentabarbital, sodium pentabarbital, secobarbital sodium, codeine, (a-bromoisovaleryl) urea, and carbromal; psychic energizers, such as 3-(2-aminopropyl) indole acetate and 3-(2-aminobutyl) indole acetate; tranquilizers, such as diazepam, chlordiazepoxide hydrochloride, reserpine, chlorpromazine hydrochloride, and thiopropazate hydrochloride; hormones, such as adrenocorticosteroids, for example, 6-methyl-prednisolone; androgenic steroids, for example, testosterone, methyltestosterone, and fluoxymesterone; estrogenic steroids, for example, estrone, estradiol and ethinyl estradiol; progestational steroids, for example, levonorgestrel, progesteron, 17a-hydroxyprogesterone and acetate, medroxyprogesterone and acetate, 19-norprogesterone, and norethindrone; thyroxine; antipyretics, such as aspirin, salicylamide, methylsalicylate, triethanolamine salicylate; morphine and other narcotic alangesics; hypoglycemic agents, for example, sulfonyl ureas such as glypizide, glyburide and chlorpropamide and insulin; antispasmodics, such as atropine, methscopolamine bromide, methscopolamine bromide with phenobarbital, antimalarials, such as the 4-aminoquinolines, 9-aminoquinolines, and pyrimethamine; adrenergic block agents, such as metoprolo; antiarthritic agents, such as sulindac; nonsteroidal anti-inflammatory agents, such as ibuprofen and naproxen; vasodilators, such as dipyridamole, isosorbide dinitrate; antihypertension agents, such as propanolol, methyldopa and prazosin; contraceptive agents, such as levonorgestrel/estradiol combination and norethindrone acetate combination; agents for treating duodenal ulcers, such as cimetidine; and nutritional agents, such as vitamins, essential amino acids, and essential fats. The above listing of pharmaceuticals is merely exemplary of the transdermally applicable pharmaceuticals. It is contemplated that any pharmaceutical can be utilized may be transdermally administered by use of this invention.

The presence of enhancing agents in the dosage units together with the pharmaceutical is often highly useful. It has been found that the presence of oleic acid as an enhancing agent in certain dosage units of this invention is highly advantageous. Other enhancing agents which are useful in this invention can be selected from the following: long-chain alkanols, long-chain alkanolic acids and their esters, ceramide, dialkyl sulfoxide, surfactants, and the like.

EXAMPLE 1

Figure 3B:
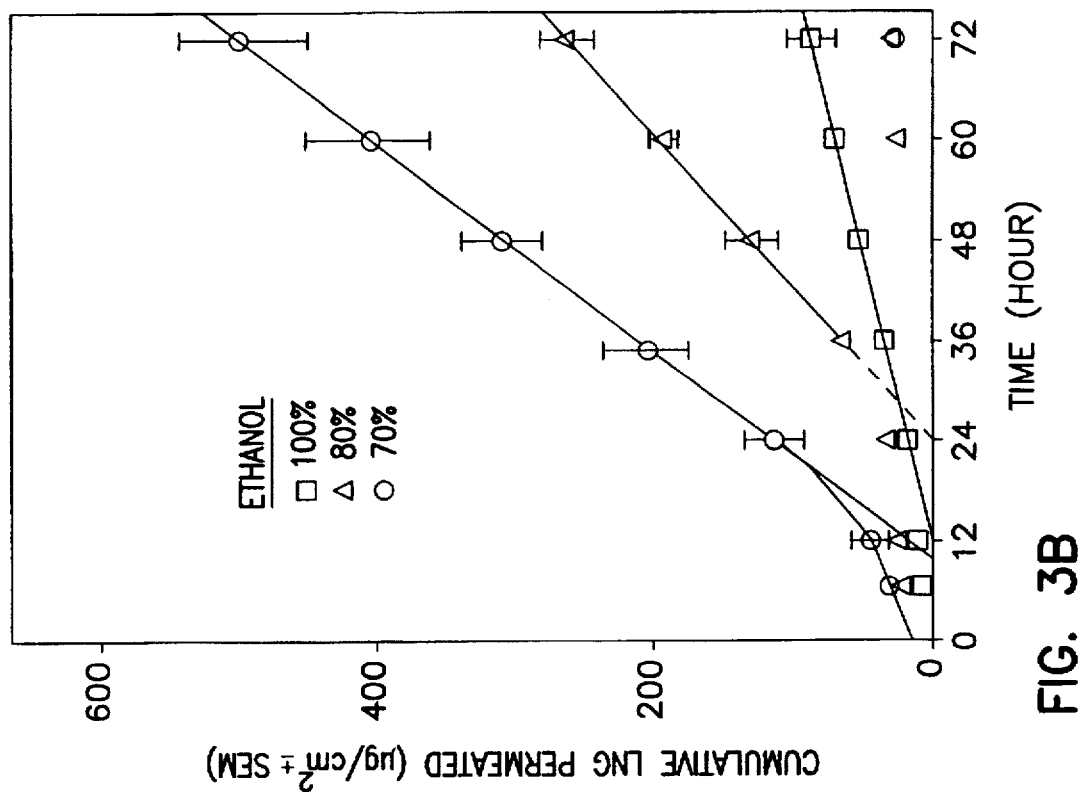
FIGS. 3A and 3B show the permeation profile of levonorgestrel as it is varied, depending upon the amount of ethanol present in a water-ethanol combination as compared to 100% water and 100% ethanol.
Figure 3A:
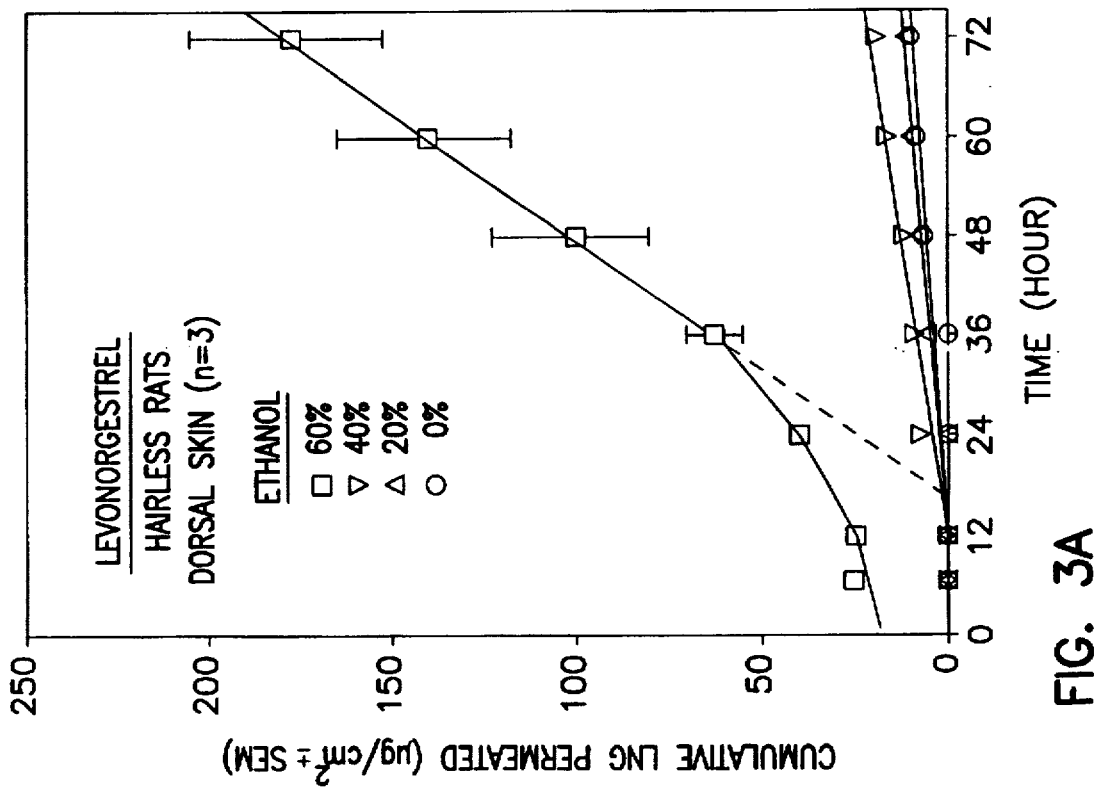
Figure 4:
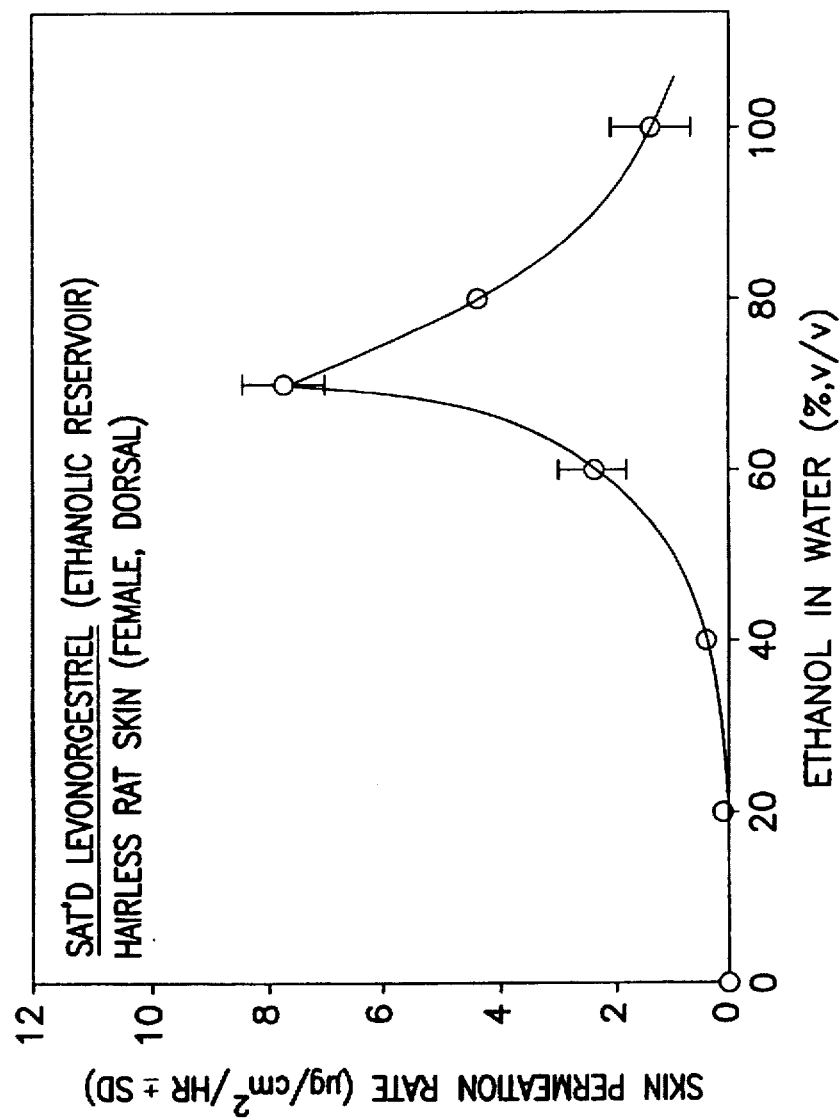
FIG. 4 shows the variation in the skin permeation rate of levonorgestrel dependent upon the concentration of ethanol in water on a volume/volume percent basis.

A dosage unit as shown in FIG. 1 is fabricated. The backing layer employed is the following. The permeability-regulating polymer membrane used is EVA, 28 percent vinyl acetate, sold by 3M Co., 50 micron thick. The skin permeation rate of levonorgestrel is controlled by using the combination of ethanol and water with varying concentration or ratio as the dissolving solvent for levonorgestrel to form solution which is placed within the reservoir as shown in FIG. 1 as drug reservoir compartment. As shown in FIG. 3, the cumulative levonorgestrel amount of permeation (mcg/cm$^2$±SEM) is varied greatly by varying the ratio of ethanol:water. It is shown that very little permeation is realized when 100 percent water is utilized as well as very low permeation is achieved with 100 percent ethanol. It is noted from the graphs of FIGS. 3A and 3B that greatly enhanced rates of permeation are realized at a ratio of ethanol:water of 60:40 and a ratio of 80:20 and 70:30. It is noted that of the ratios shown, the highest cumulative levonorgestrel permeation rate is realized by utilizing the 70:30 ratio. The data with respect to the difference in the skin permeation of levonorgestrel as a function of the ethanol:water ratio are shown on the graph of FIG. 4 wherein the skin permeation rate of levonorgestrel in mcg/cm$^2$/hr. ±S.D. vs. ethanol:water ratio on a volume/volume basis is shown.

The following table shows the dependence of the skin permeation rate of levonorgestrel and enhancement based on the ethanol:water ratio in the reservoir solution used which contains the levonorgestrel.

| Dependence of the Skin Permeation Rate of Levonorgestrel and Enhancement on the Volume Fraction of Ethanol in Reservoir Solution | | | |
|---|---|---|---|
| Reservoir Solution[1] (% V/V) | | Skin Permeation Rate[2] | Enhancement[3] |
| Ethanol | Water | (mcg/cm$^2$/hr ± S.D.) | Factor |
| 0 | 100 | 0.03 (0.01) | 1.0 |
| 20 | 80 | 0.09 (0.03) | 3.0 |
| 40 | 60 | 0.47 (0.02) | 15.7 |
| 60 | 40 | 2.40 (0.68) | 80.0 |
| 70 | 30 | 7.69 (0.94) | 256.3 |
| 80 | 20 | 4.01 (0.33) | 133.7 |
| 100 | 0 | 1.33 (0.55) | 44.3 |

[1]Saturated levonorgestrel solution
[2]Dorsal skin (n = 3 each) freshly excised from hairless rat.
[3]Compared to the skin permeation rate of levonorgestrel from reservoir solution having 100% (V/V) of water as the vehicle.

Figure 5:
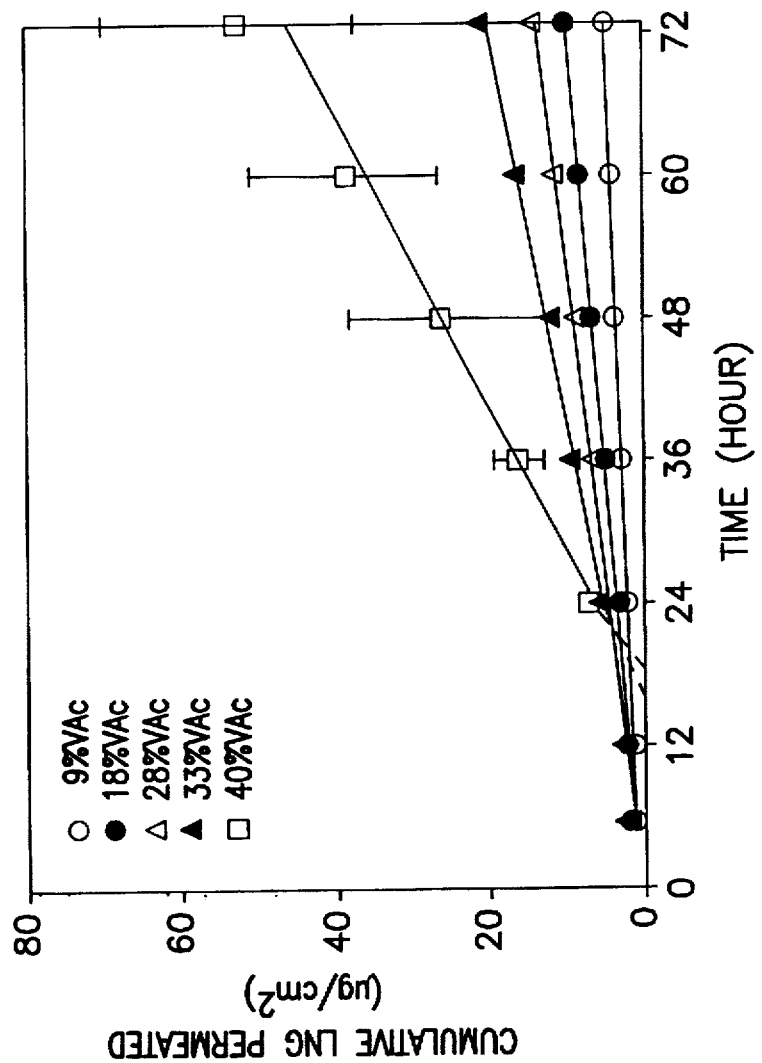
FIG. 5 is a graph showing the difference in levonorgestrel permeation rate depending upon the weight percent of vinyl acetate in the permeability-regulating (ethylene/vinyl acetate) copolymer membrane in a dosage unit as shown in FIGS. 1 and 2.

FIG. 5 shows the difference in the levonorgestrel permeation rate depending upon the content of vinyl acetate in the permeability-regulating polymer membrane as shown in FIG. 1 as permeability-regulating polymer membrane. It is shown that as the weight fraction of vinyl acetate in the permeability-controlling membrane increases from 9 percent to 40 percent, the levonorgestrel permeation rate increases.

Figure 6:
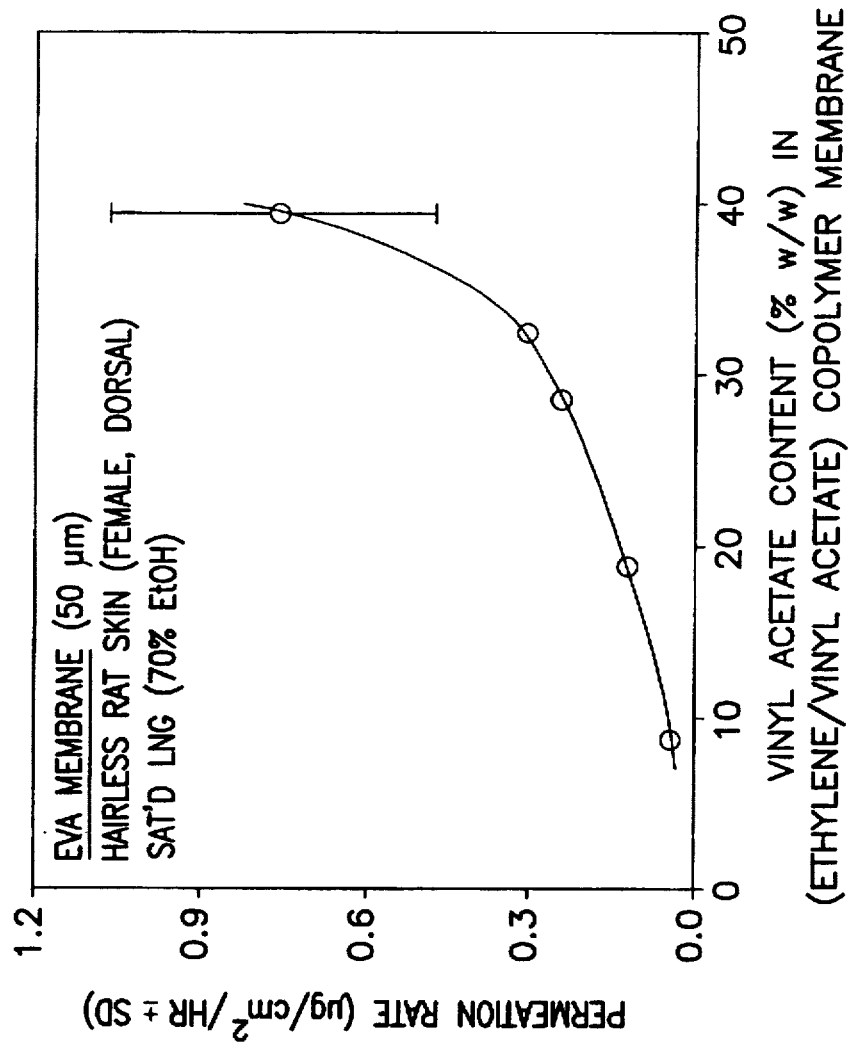
FIG. 6 is a graph showing the effect of the vinyl acetate content in the permeability-regulating membrane consisting of a (ethylene/vinyl acetate) copolymer upon the permeation rate of levonorgestrel across hairless rat skin.

The particular permeability-regulating membrane utilized in this experiment is an (ethylene/vinyl acetate) co-polymer as shown in FIG. 6. The rates of transdermal permeation (in mcg/cm$^2$/hr±S.D.) of levonorgestrel in the hairless rat skin test utilizing a 50 micron (ethylene/vinyl acetate) copolymer membrane having variation in the weight fractions of vinyl acetate from 9% to 40% from a saturated levonorgestrel donor solution containing the ratio of ethanol:water of 70:30.

Figure 7:
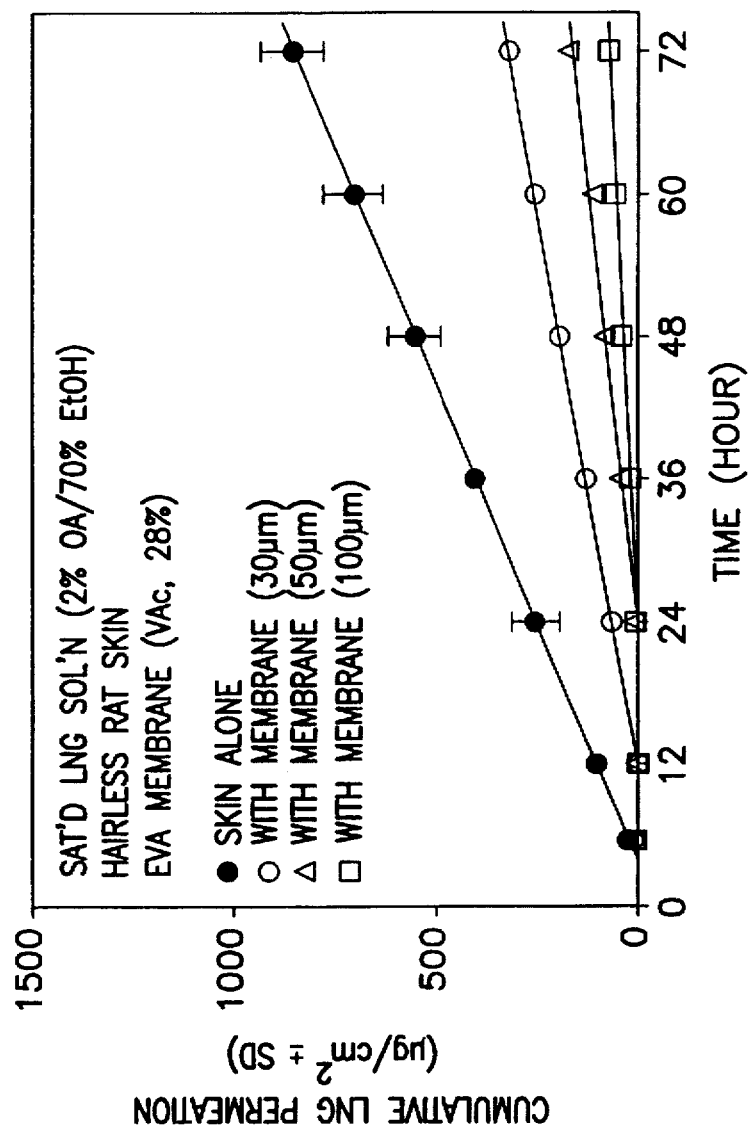
FIG. 7 is a graph which shows the difference in the skin permeation profile of levonorgestrel vs. the thickness of a permeation-regulating (ethylene/vinyl acetate) copolymer membrane in a dosage unit of the type shown in FIGS. 1 and 2 as compared with the permeation rate wherein no membrane is in contact with the skin.

FIG. 7 shows the difference in cumulative levonorgestrel permeation vs. thickness of the permeability-regulating (ethylene/vinyl acetate) copolymer membrane shown in FIG. 1, along with a comparison with the rate of permeation wherein no membrane is utilized, i.e., skin alone. A saturated levonorgestrel solution of ethanol:water of 70:30 on a V/V basis. Two percent of oleic acid was utilized. The membrane polymer contained 28% vinyl acetate. It is noted that differences in the thickness of membrane varied from 30 microns to 50 microns and 100 microns. It is noted that substantially more levonorgestrel was absorbed transdermally when a 30 micron membrane was utilized and that the lowest level of permeation was observed when the 100 micron membrane was used.

Figure 8:
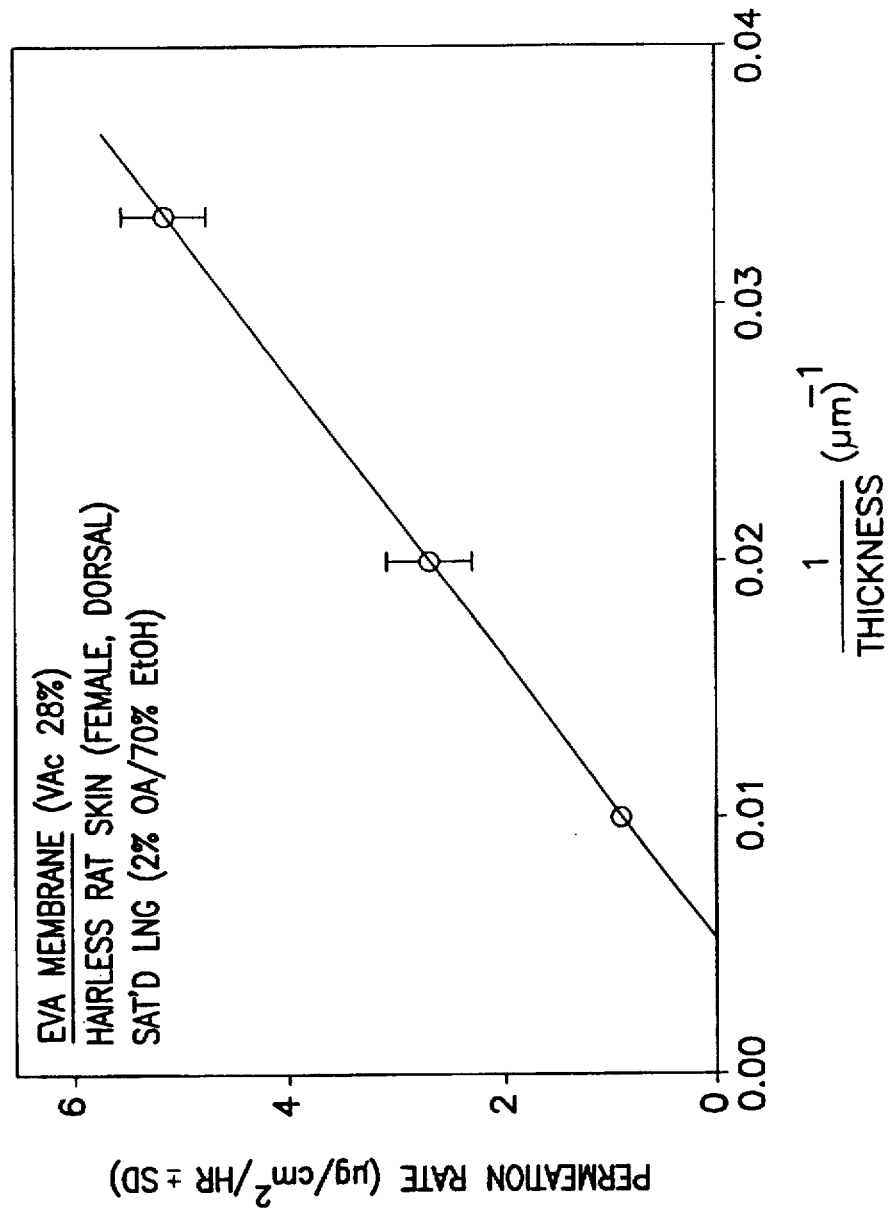
FIG. 8 is a graph which shows the relationship between the skin permeation rate of levonorgestrel across the permeability-regulating membrane utilizing a (ethylene/vinyl acetate) copolymer membrane containing 28% vinyl acetate and wherein the macroreservoir solution contains 70% ethanol, as solubilizer, 2% oleic acid, as skin permeation-enhancing agent, and 28% water on a volume/volume basis. The dosage unit utilized in this evaluation is of the type shown in FIGS. 1 and 2.

FIG. 8 shows the relationship of the permeation rate of levonorgestrel across the permeability-regulating polymer membrane utilizing a (ethylene/vinyl acetate) membrane containing 28 percent vinyl acetate and the reservoir solution containing 70% ethanol and 2% oleic acid and the remainder being water. It shows that a higher rate of permeation is obtained utilizing the 30 micron thickness and that a higher rate was obtained using a 50 micron thickness than was obtained with the 100 micron thickness.

Figure 9:
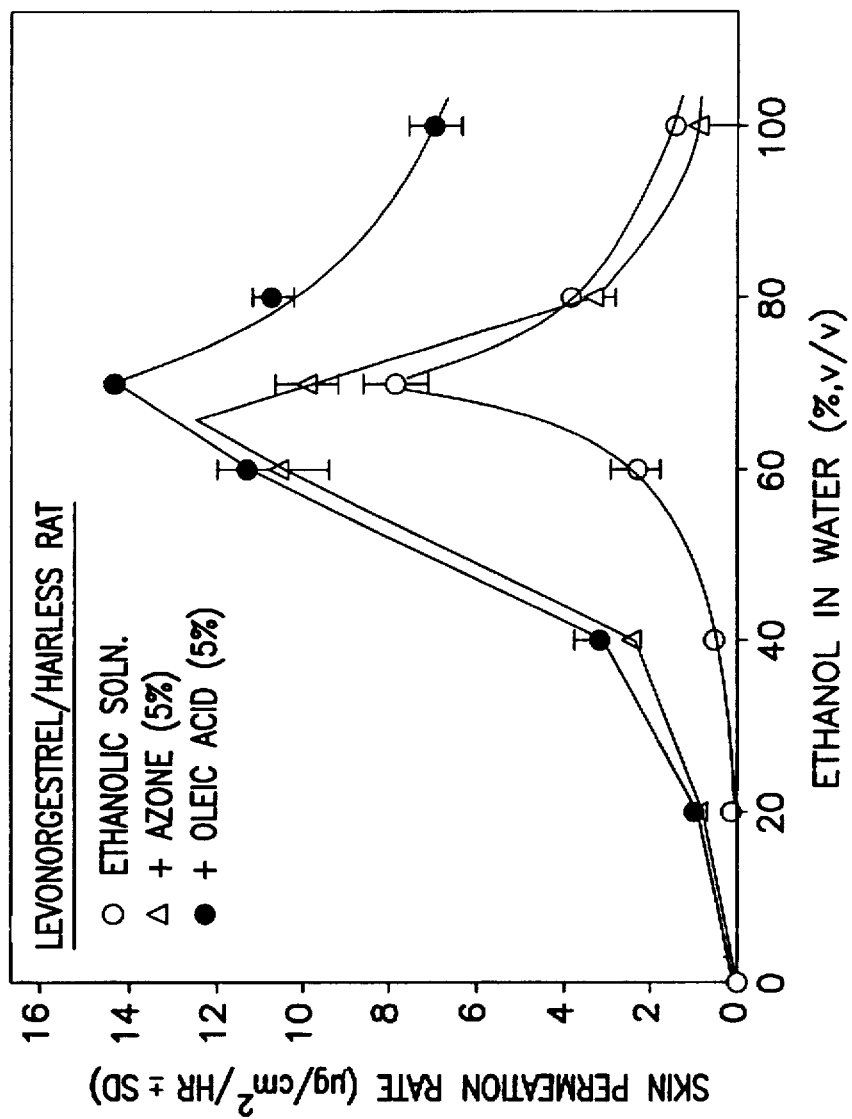
FIG. 9 is a graph which shows the skin permeation rate of levonorgestrel (in mcg/cm$^2$/hr) from a macroreservoir solution containing varying ratios of ethanol and water on a v/v basis and also shows how the absorption is affected by the presence of five percent of two different skin permeation-enhancing agents. The dosage unit utilized in this evaluation is of the type shown in FIGS. 1 and 2.

FIG. 9 shows the rate of skin permeation of levonorgestrel (in $mcg/cm^2/hr \pm S.D.$) from a reservoir solution having varying ratios of ethanol:water on a V/V basis. Reservoir solution contains 5 percent of either azone or 5 percent oleic acid as an enhancer as compared to a reservoir solution containing neither of the enhancing agents. In each case it is shown that the best skin permeation rate is obtained in the range of 60 to 80 percent ethanol. When utilizing 100 percent ethanol with no enhancing agent, about 2 mcg of levonorgestrel has been administered per hour per $cm^2$.

Figure 10:
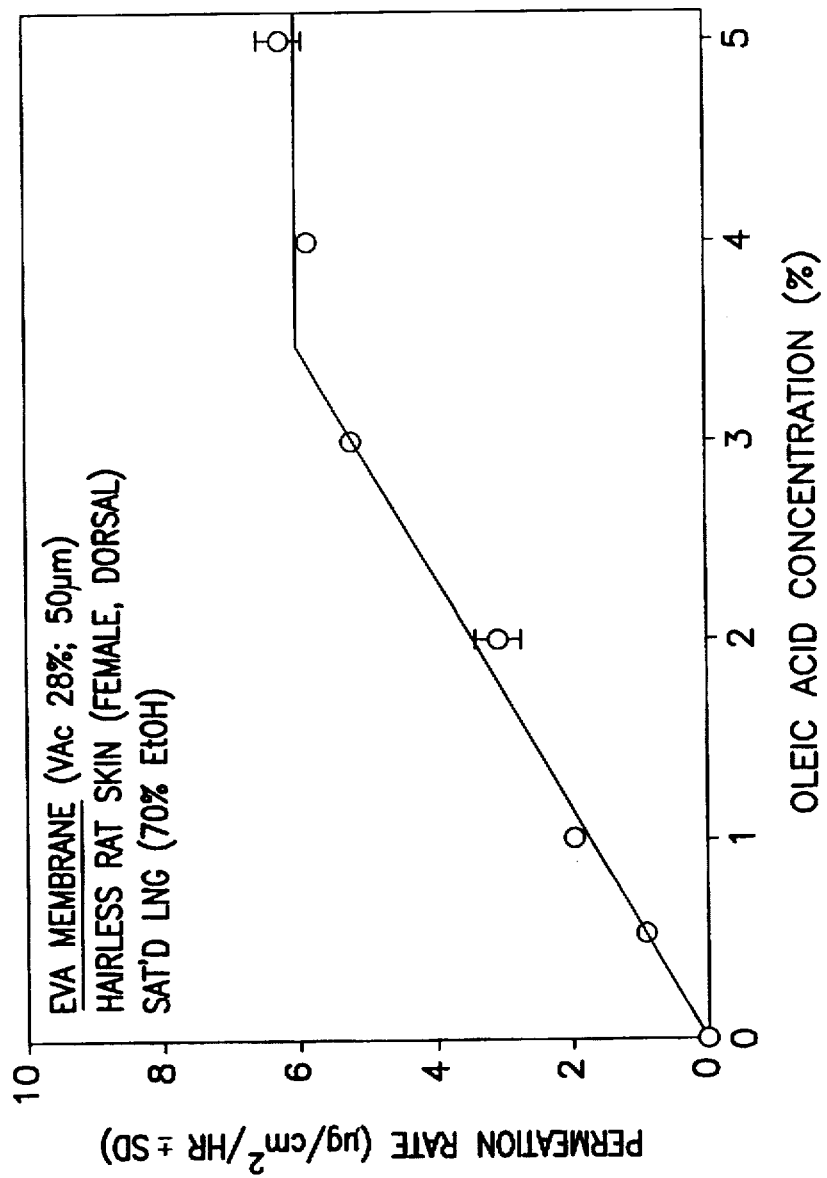
FIG. 10 is a graph which shows the change in skin permeation rate of levonorgestrel from a saturated levonorgestrel reservoir solution having a 70:30 ethanol:water ratio on a V/V basis. The dosage unit used is of the type shown in FIGS. 1 and 2. The vinyl acetate content in the permeability-controlling (ethylene/vinyl acetate) copolymer membrane is 28% and the thickness of the membrane is 50 microns. The rate of permeation is shown to increase as the concentration of oleic acid (as the skin permeation-enhancing agent) is increased.

FIG. 10 shows the change in permeation rate (on a $mcg/cm^2/hr$ basis) from a saturated levonorgestrel reservoir solution having a ratio of ethanol:water of 70:30 utilizing a permeability-regulating membrane as shown in FIG. 1 wherein the vinylacetate content is 28% and the thickness is 50 microns. The rate of transdermal absorption is shown vs. the concentration of oleic acid as the enhancing agent.

Figure 11:
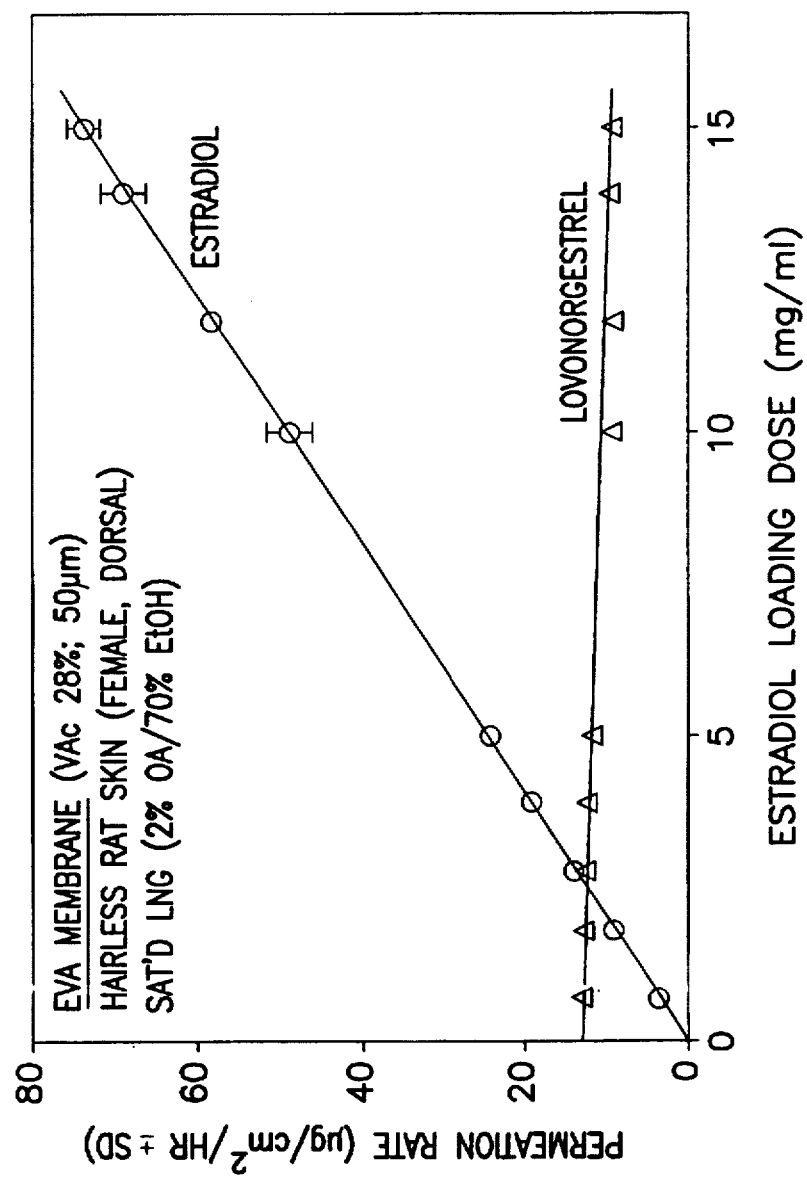
FIG. 11 is a graph showing the effect of estradiol loading dose on the permeation rate across the hairless rat skin covered with permeability-regulating (ethylene vinyl acetate) copolymer membrane wherein the vinyl acetate content is 28 percent and the thickness of the membrane is 50 microns. Hairless rat skin was utilized in this evaluation. The reservoir solution used is a saturated levonorgestrel solution wherein the ethanol concentration is 70 percent and the concentration of oleic acid as the skin permeation-enhancing agent is 2 percent. Permeation rates are shown for estradiol and levonorgestrel, in which permeation rate of estradiol varies as a function of the loading dose of estradiol in the solution. A dosage unit of the type shown in FIG. 1 is utilized in this evaluation.

FIG. 11 shows the effect of estradiol loading dose on the permeation rates of levonorgestrel and estradiol across a permeability-regulating (ethylene/vinyl acetate) membrane wherein the vinyl acetate content is 28% and the thickness thereof is 50 microns. Utilized in this evaluation was the hairless rat skin test as described above. The reservoir solution was a saturated levonorgestrel solution wherein the ethanol concentration is 70% and the concentration of oleic acid as the enhancing agent is 2%. Permeation rates (on the basis of $mcg/cm^2/hr$) are shown for estradiol and levonorgestrel. In the graph, the loading dose of estradiol is varied from one to 15 milligrams/milliliter in the reservoir solution.

Figure 12:
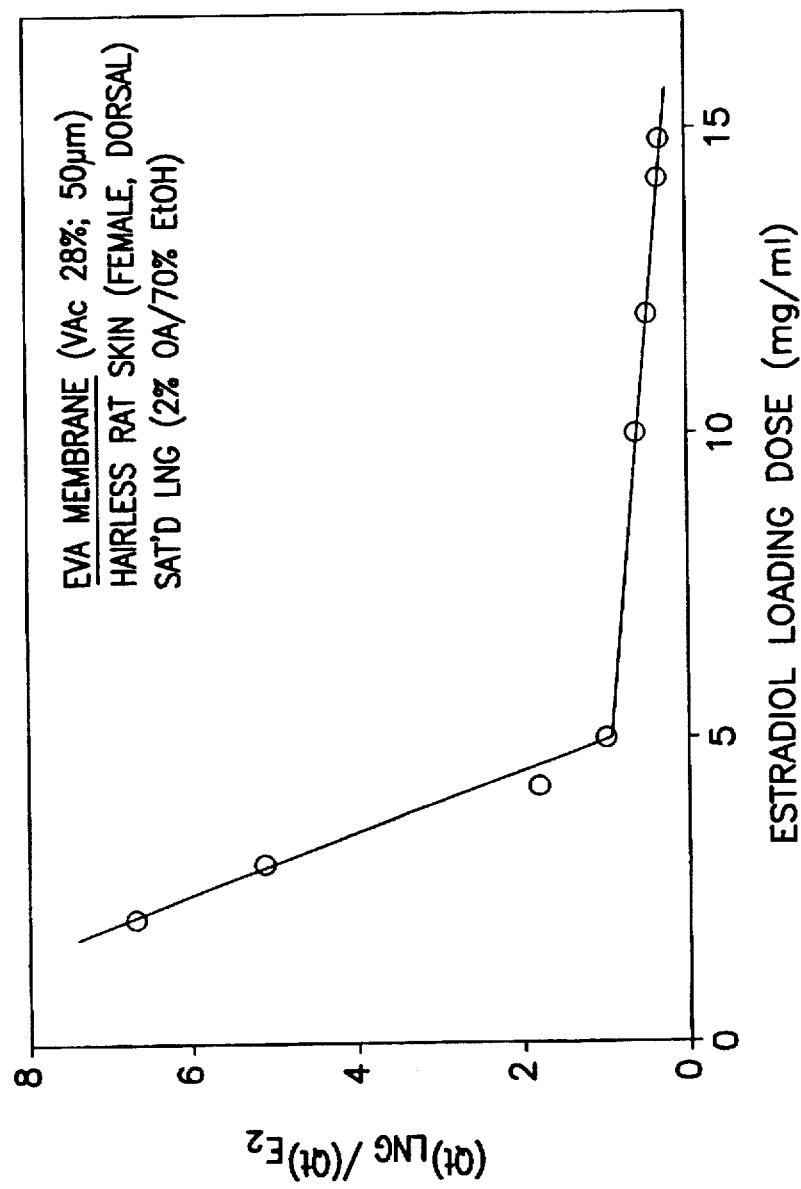
FIG. 12 is a graph showing the effect of estradiol loading dose on the ratio of skin permeation rates of levonorgestrel over estradiol. In the evaluation, a permeability-regulating (ethylene/vinyl acetate) membrane having a vinyl acetate content of 28 percent and a thickness of 50 microns is used. The hairless rat skin test is utilized as well as the saturated levonorgestrel concentration in 70 percent ethanol and 2 percent oleic acid, as the enhancer, are used.

FIG. 12 is a curve showing the ratio of the cumulative transdermal absorption of levonorgestrel over the cumulative transdermal absorption of estradiol. The data in the graph show that as the loading dose of estradiol is increased, the permeation rate ratio of levonorgestrel over estradiol varies from greater than unity to less than unity. The permeation rate ratio of levonorgestrel over estradiol utilizing a 2 milligram/milliliter loading of estradiol is about 6.5 and at 5 milligram/milliliter loading of estradiol, the permeation rate ratio of levonorgestrel over estradiol is reduced to about 1 and is further reduced to about 0.2 at an estradiol loading of 15 milligrams/milliliter.

Figure 13:
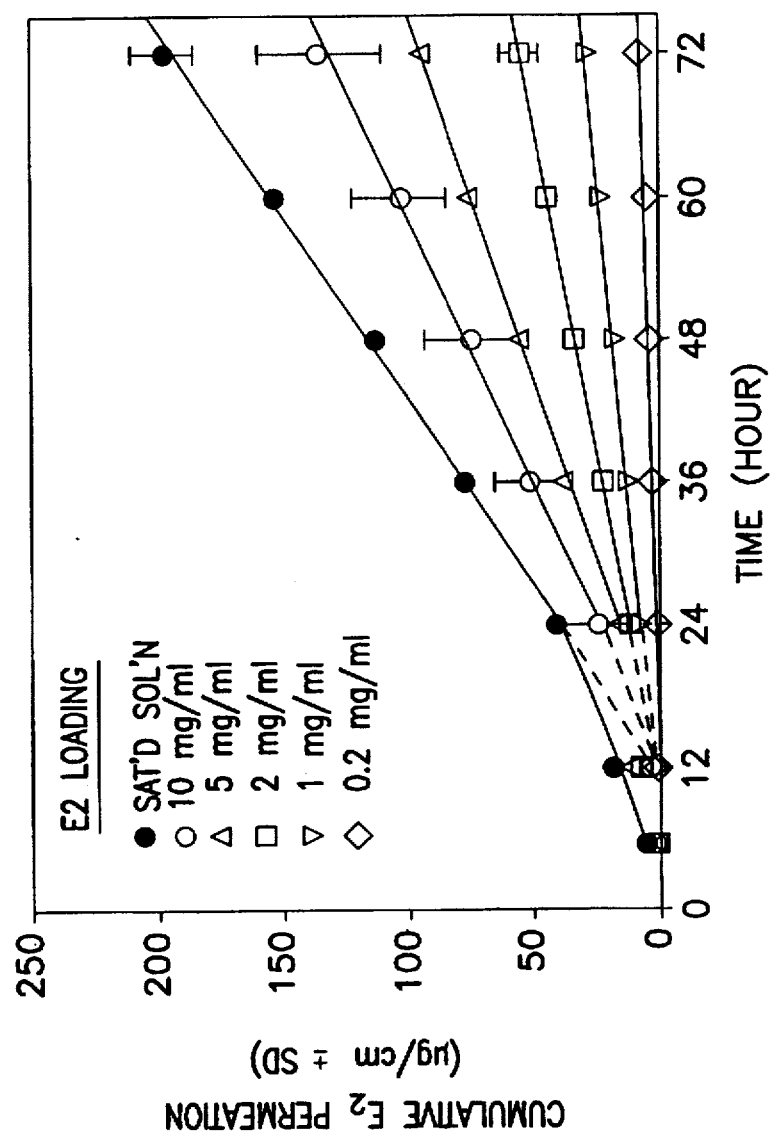
FIG. 13 is a graph which shows estradiol permeation profiles from a dosage unit such as the one shown in FIG. 1 utilizing the test procedure in which human cadaver skin is covered with a permeability-regulating (ethylene/vinyl acetate) copolymer membrane. The skin permeation of estradiol is from a reservoir solution having levonorgestrel at saturation concentration. Various estradiol concentrations are utilized in the comparative testing, with estradiol loadings varying from 0.2 to 10 milligrams/milliliter and to saturation concentration. A dosage unit of the type shown in FIG. 1 is used.

FIG. 13 shows the cumulative estradiol permeation (based on $mcg/cm^2/hr \pm S.D.$) utilizing a dosage unit such as that shown in FIG. 1 utilizing human cadaver skin test procedure. The transdermal absorption of estradiol is from a reservoir solution saturated with levonorgestrel. Various estradiol concentrations are utilized in the comparative testing, varying from an estradiol loading which is a saturated solution to 10, 5, 2, 1 and 0.2 milligrams/milliliter of estradiol loading. Utilizing a dosage unit such as that shown in FIG. 1, cumulative levonorgestrel permeation (based on $mcg/cm^2 \pm S.D.$) is shown. A permeation profile of levonorgestrel across a permeability-regulating membrane which is an (ethylene/vinyl acetate) membrane containing 28 percent vinyl acetate and utilizing human cadaver test procedure.

Figure 14:
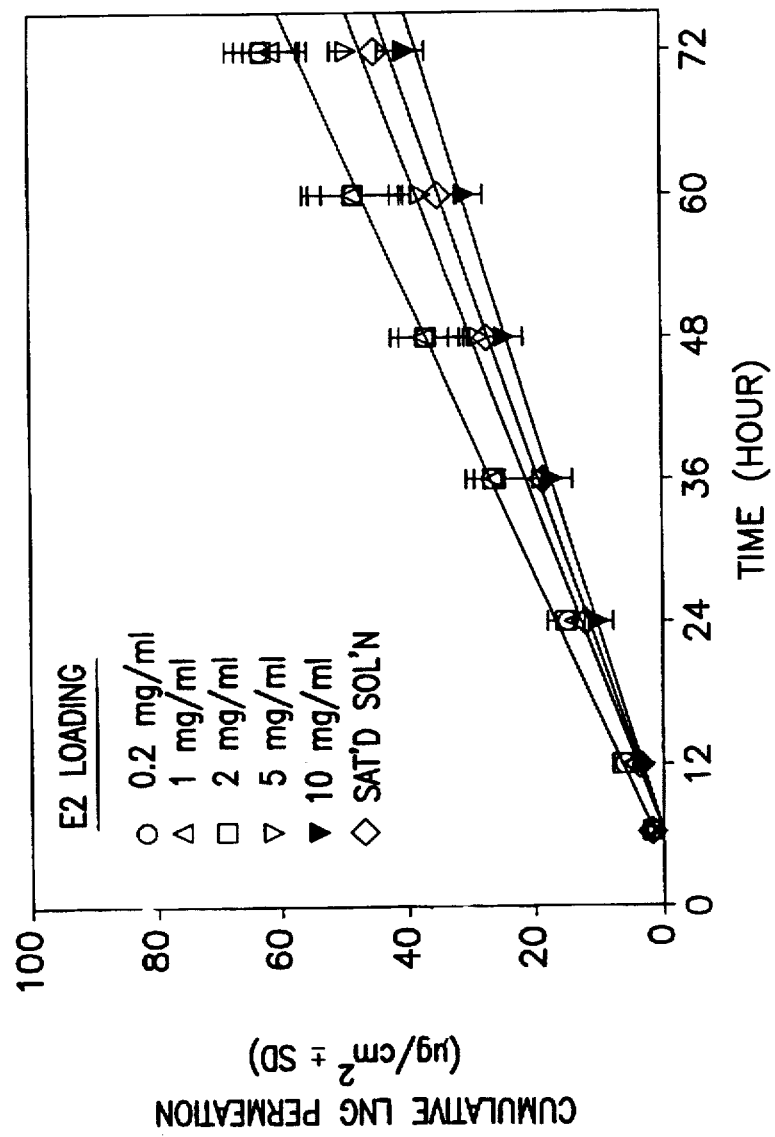
FIG. 14 is a graph which shows a permeation profile of levonorgestrel across a permeability-regulating (ethylene/vinyl acetate) copolymer membrane covered human cadaver skin. The dosage unit utilized is of the type shown in FIG. 1. Varying estradiol concentrations are used in the reservoir solution varying from 0.2 mg/ml to saturation.

FIG. 14 shows a permeation profile of levonorgestrel across an (ethylene/vinyl acetate) membrane-covered human cadaver skin. Various estradiol loadings are used in the reservoir solution varying from 0.2 mg/ml to saturation.

Figure 15:
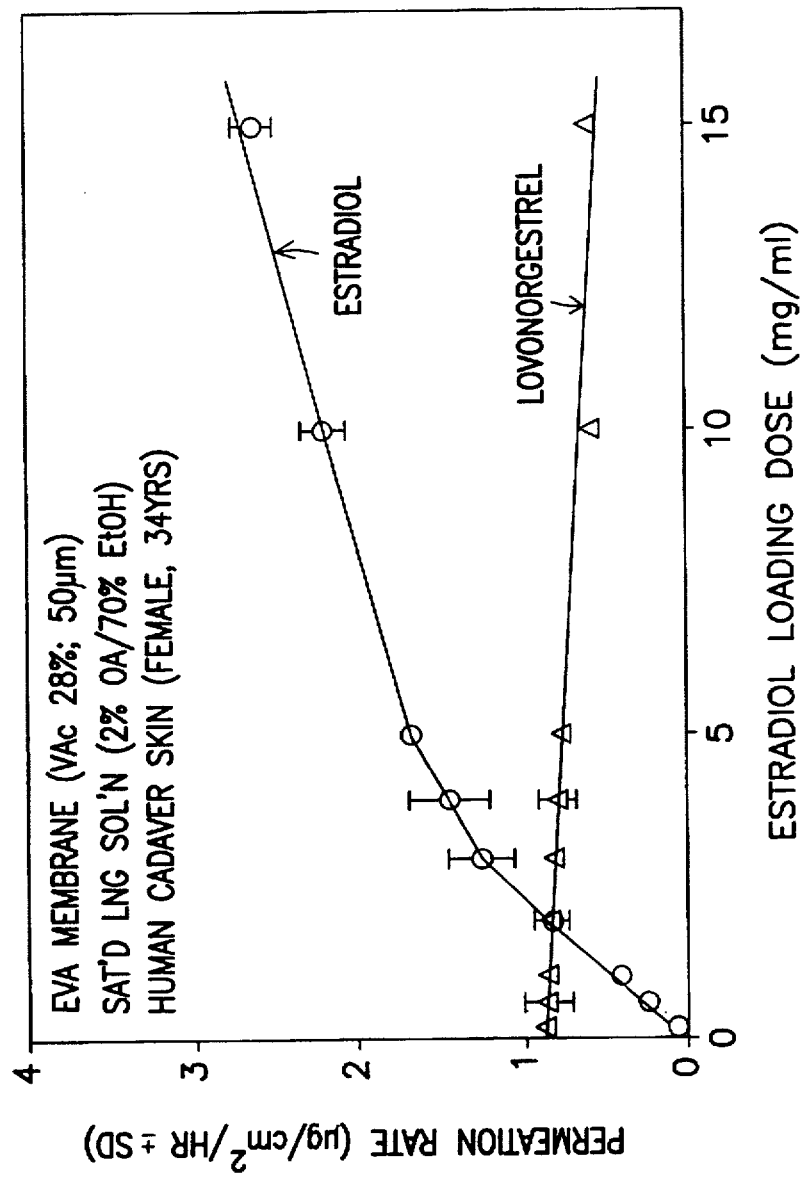
FIG. 15 is a graph showing the effect of estradiol loading in a dosage unit as shown in FIG. 1 on the permeation rates of estradiol and levonorgestrel across a permeability-controlling membrane utilizing an (ethylene/vinyl acetate) copolymer membrane. The evaluation is done in the absorption test utilizing human skin. The donor solution contained in the macroreservoir is saturated with levonorgestrel, contains 2 percent oleic acid as an enhancing agent and has 70 percent ethanol and 28 percent water.

FIG. 15 shows a dosage unit as shown in FIG. 1 wherein the reservoir solution has varying levels of estradiol loading and the permeation rates of levonorgestrel and estradiol have been varied depending upon estradiol loading. A permeability-regulating (ethylene/vinyl acetate) membrane is utilized as the permeation-controlling membrane shown in FIG. 1. The human cadaver skin test was utilized. The data show the change in the permeation rates (based upon $mcg/cm^2/hr \pm S.D.$) of both estradiol and levonorgestrel from a reservoir solution consisting of saturated levonorgestrel with a ratio of ethanol:water at 70:28 by volume. The reservoir solution also contains 2% of oleic acid. The permeability-regulating membrane used comprises 28% vinyl acetate and has a thickness of 50 microns. The estradiol loading varies from zero to 15 milligrams/milliliter. It is shown that the permeation rate for levonorgestrel at zero percent estradiol loading in this system is about 1 and slightly declines to about 0.7 $mcg/cm^2/hr$ at 15 milligrams/milliliter of estradiol.

Figure 16:
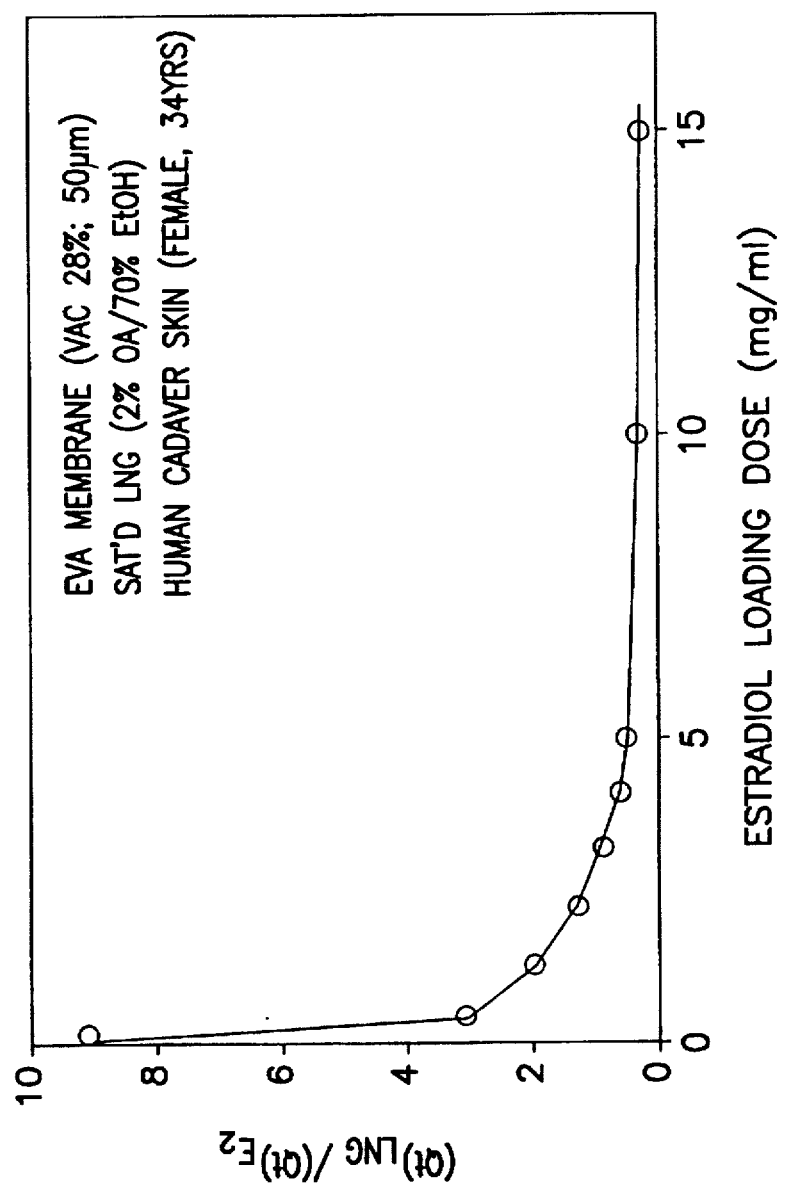
FIG. 16 is a graph showing the effect of estradiol loading on the ratio of the permeation rates of levonorgestrel over estradiol. The permeability-controlling membrane of (ethylene/vinyl acetate) copolymer is utilized wherein the vinyl acetate content is 28 percent and the thickness is 50 microns. Levonorgestrel is present at saturated condition. Two percent oleic acid and 70 percent ethanol are utilized in the aqueous reservoir solution. Human cadaver skin is used in the absorption test.

FIG. 16 shows a graph wherein the effect of estradiol loading on permeation rate ratio of levonorgestrel over estradiol. The graph shows that the permeation rate ratio is greatly reduced depending upon the loading dose of estradiol. The permeability-regulating (ethylene/vinyl acetate) membrane utilized has 28 percent vinyl acetate and has a thickness of 50 microns. The reservoir solution, which is saturated with levonorgestrel, has 70 percent ethanol and 2 percent oleic acid content. The human cadaver skin test is utilized.

Figure 17:
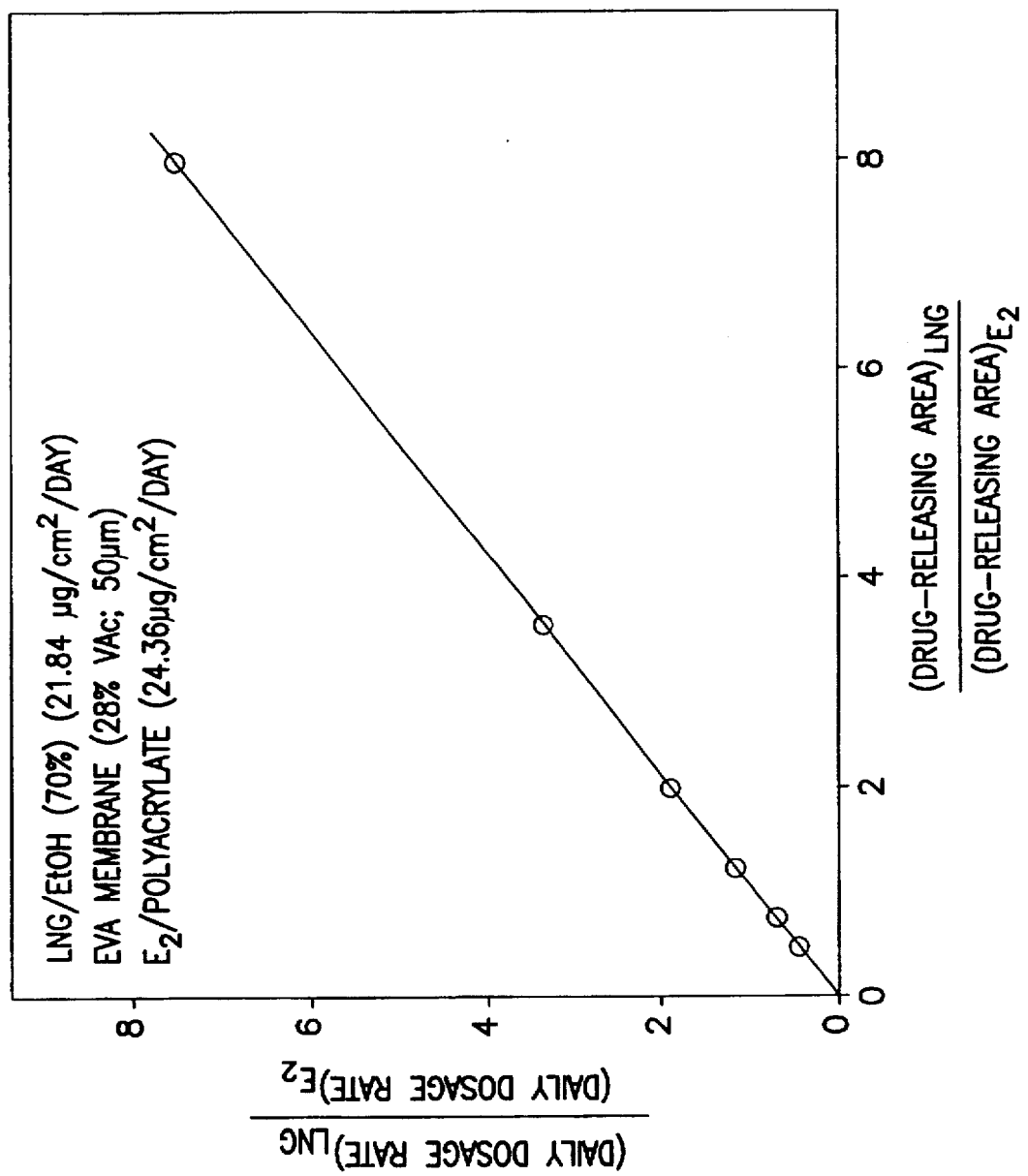
FIG. 17 is a graph showing the effect of variation in the ratio the pharmaceutical-releasing area in a dosage unit of the type shown in FIG. 2 on the dosage rate ratio of levonorgestrel/estradiol. Levonorgestrel is present in the macroreservoir wherein the reservoir solution is 70 percent ethanol and 30 percent water. The permeability-controlling membrane is a (ethylene vinyl acetate) membrane having 28 percent vinyl acetate and a thickness of 50 microns. Estradiol is present in the peripheral ring reservoir as a microreservoir of estradiol wherein the polymeric material used is a polyacrylate.

FIG. 17 is a graph showing the effect of drug releasing area on dosage rate ratio of levonorgestrel over estradiol. A dosage unit of the type shown in FIG. 2 is utilized. The reservoir solution in drug-reservoir compartment A is a saturated levonorgestrel solution wherein the ethanol:water has a ratio of 70:30 and the permeation rate of levonorgestrel is 21.84 $mcg/cm^2/day$. The permeability-regulating membrane is an (ethylene/vinylacetate) membrane containing 28 percent vinyl acetate and having a thickness of 50 microns. The permeation rate of estradiol in the polyacrylate adhesive used to make the peripheral ring as shown as drug-reservoir compartment B in the FIG. 2 dosage unit is 24.36 $mcg/cm^2/day$. As the area of the pharmaceutical-releasing area pertaining to levonorgestrel is increased over the pharmaceutical-releasing area of estradiol, the ratio of daily dosage rate of levonorgestrel over the daily dosage rate of estradiol is increased. It is shown, for example, that the ratio of the daily dosage rate of levonorgestrel/daily dosage rate of estradiol changes from about 2 when the ratio of the pharmaceutical-releasing area of levonorgestrel/pharmaceutical-releasing area of estradiol is 2 to about a daily dosage rate of levonorgestrel/daily dosage rate of estradiol of about 7.5 when the permeability-releasing area of levonorgestrel/pharmaceutical-releasing area of estradiol is 8. The following table compares the skin permeation rates of estradiol and levonorgestrel across permeability-regulating membranes of different compositions when utilized in the human cadaver skin test.

Comparison Between Skin Permeation Rates of Estradiol and Levonorgestrel Across Various Polymeric Membranes Applied on Human Cadaver Skin[1]

| Membrane | Thickness (micron) | Permeation Rate[2] (mcg/cm$^2$hr ± S.D.) | |
| --- | --- | --- | --- |
| | | Estradiol | Levonorgestrel |
| (Ethylene/vinyl acetate) Copolymer[3] | 51 | 0.17 (0.02) | 0.64 (0.16) |
| Polyethylene[4] | 51 | 0.93 (0.18) | 3.01 (0.58) |
| Silicone | 300 | 0.00 | 0.17 (0.02) |

[1]Human cadaver skin (female, 34 years old; thigh region) covered with polymeric membrane.
[2]From a saturated solution of levonorgestrel, in 70% ethanol and 2% oleic acid, which contains 0.5 mg/ml of estradiol.
[3]3M Co. (VAc, 28% W/W); 51 micron)
[4]3M Co. (microporous, 18 micron; void volume, 78%)

EXAMPLE 2

A bi-regional transdermal drug delivery system which can simultaneously deliver a progestin, such as levonorgestrel (LNG) and an estrogen, such as 17-beta-estradiol (E2) from its central and peripheral regions, respectively, is fabricated by using the following processes and equipment:

Thoroughly mix 0.52 part of E2, 10.81 parts of oleic acid (OA) and 88.67 parts of polyacrylate adhesive solution (Duro-Tak 80-1054, by National Starch and Chemical Co., New Jersey, which contains 36% of solid) by weight in a container to form a homogeneous E2/OA adhesive solution. This solution is coated onto a silicone-coated release liner (Akrosil B2M) by a specially-designed pattern coating device to form a circular ring of peripheral region. This peripheral region has an inner and outer radius of 1.59 cm and 2.18 cm, respectively, which gives a 0.59 cm width and 7 sq cm to the area of the region. The wet thickness of the coating of this adhesive solution is controlled at 500 microns which is then cured in an oven at 60° C. for 10 minutes to form the dried matrix of peripheral region about 200 microns thickness. The peripheral region obtained by this fabrication process is thereafter named Intermediate Product A (IP-A).

Oleic acid, ethanol and water are mixed thoroughly at the weight ratio of 1:37:14 to form a homogeneous hydroalcoholic solution system (HASS). An amount of 0.0036 part by weight of LNG is dissolved in 1.000 part by weight of HASS to form a homogeneous LNG/HASS solution. An amount of 400 microliters of LNG/HASS solution is carefully applied by a dispenser onto a piece of 50 micron-thick heat-sealable (ethylene/vinyl acetate) membrane (EVA, 28% vinyl acetate, by 3M Co.) which was precast on the siliconized paper release liner. The dispensed LNG/HASS solution is quickly covered with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine sealing process is performed at 370° F. and 50 psi for 1 (one) second of dwell time. The central region (7 sq cm in size) obtained by this process is designated Intermediate Product B (IP-B).

To complete the fabrication of the biregional transdermal drug delivery system, IP-A is carefully laminated on the IP-B by a laminating device. The final product (15 sq cm in size), which is in the form of a transdermal patch, can be cut out by a die cutter.

The novel design of this patch product will allow the two drugs to be delivered simultaneously from a single unit of transdermal patch. LNG is delivered from the central region, while E2 is delivered from the peripheral region. In addition to changing the formulation ingredients in each region, the daily delivery rate of each drug can be altered by changing the relative size of the surface area of the two regions. This final product has the equal size of surface area (7 cm. sq) for the central and peripheral regions to allow desired amount of LNG and E2, respectively, to be delivered. In the in-vitro skin permeation study, this final product is found to give permeation rate of 0.62 and 0.30 mcg/sq cm/hr of LNG and E2, respectively, which can be translated into the daily delivery rate of 104.2 mcg of LNG and 50.4 mcg of E2.

EXAMPLE 3

A bi-regional transdermal drug delivery system, which can simultaneously deliver a combined dosage of progestin, such as levonorgestrel (LNG), and estrogen, such as 17-beta-estradiol (E2), from its central region, is fabricated by using the following processes and equipment:

Thoroughly mix 5.06 parts of Ceraphil 31 (by Van Dyk/ New Jersey), 94.94 parts of polyacrylate adhesive solution (Duro-Tak 80-1054, by National Starch and Chemical Co./ New Jersey, which contains 48% of solid) by weight in a container to form a homogeneous adhesive solution. This solution is coated onto a silicone-coated release liner (Akrosil B2M) by a specially-designed pattern coating device to form a circular ring of peripheral region. This peripheral region has an inner and outer radius of 1.59 cm and 2.18 cm, respectively, which gives 0.59 cm to the width and 7 sq cm to the area of the region. The wet thickness of the coating of this adhesive solution is controlled at 500 microns which is then cured in an oven at 60° C. for 10 minutes to form the dried matrix of peripheral region about 220 microns thick. The peripheral region obtained by this process is designated Intermediate Product A (IP-A).

Oleic acid, ethanol and water are mixed thoroughly at the weight ratio of 1:37:14 to form a homogeneous hydroalcoholic solvent system (HASS). An amount of 0.0010 part by weight of E2 and 0.0036 part by weight of LNG are dissolved in 1.000 part by weight of HASS to form a homogeneous E2/LNG/HASS solution. An amount of 400 microliters of E2/LNG/HASS solution is carefully applied by a dispenser onto a piece of 50 micron-thick heat-sealable (ethylene/vinyl acetate) membrane (EVA, 28% vinyl acetate, by 3M Co.) which was precast on the siliconized paper release liner. The dispensed E2/LNG/HASS solution is quickly covered with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. The sealing process is performed at 370° F. and 50 psi for 1 (one) second of dwell time. The central region (7 sq cm in size) obtained by this process is designated Intermediate Product B (IP-B).

To complete the fabrication of the biregional transdermal drug delivery system, IP-A is carefully laminated onto the IP-B by a laminating device. The final product (15 sq cm in size), which is in the form of a transdermal patch, is cut out by a die cutter.

The novel design of this patch product will allow the two drugs to be delivered simultaneously from a single transdermal patch. Both E2 and LNG are delivered from the central region of this biregional transdermal patch. The peripheral region, which is made up of a pressure sensitive adhesive that contains a water-repelling tackifier (Ceraphil 31) composition: lauryl lactate 50–60 percent, myristyl lactate 15–20 percent, lauryl alcohol 10–20 percent, myristyl alcohol 2–10 percent will ensure the central region to have good contact with skin. In addition to varying the thickness and/or the vinyl acetate content of the EVA membrane, the daily delivery rate of each drug can be altered by changing their concentration in the HASS that is sealed in the central region. This dosage unit has the equal size of surface area (7 sq cm) for the central and peripheral regions to allow desired doses of LNG and E2 to be delivered. In the in-vitro skin permeation study, this final product was found to give permeation rate of 0.62 and 0.26 mcg/sq cm/hr of LNG and E2, respectively, which can be translated into the daily delivery rate of 104.2 mcg of LNG and 43.7 mcg of E2. Another dosage unit formulation in which the central region is made up of 0.005 part by weight of E2 and 0.001 part by weight of LNG in 1.000 part by weight of HASS, is found to give human cadavers kin permeation rate of 1.63 and 0.25 mcg/sq cm/hr, respectively, in an in vitro test. These skin permeation rates of E2 and LNG can be translated into daily delivery rate of 273.8 and 42.0 mcg/day, respectively.

EXAMPLE 4

A bi-regional transdermal drug delivery system which can simultaneously deliver a progestin, such as levonorgestrel (LNG), and an estrogen, such as 17-beta-estradiol (E2), from its central and peripheral region, respectively, is fabricated by using the following processes and equipment:

Thoroughly mix 0.48 part of E2, 9.68 parts of oleic acid (OA) and 89.84 parts of polyacrylate adhesive solution (Duro-Tak 80-1054, by National Starch and Chemical Co., New Jersey, which contains 36% of solid) by weight in a container to form a homogeneous E2/OA adhesive solution. This solution is coated onto a silicone-coated release liner (Akrosil B2M) by a specially-designed pattern coating device to form a circular ring of peripheral region. This peripheral region has an inner and outer radius of 0.9 cm and 1.78 cm, respectively, which provides a 0.88 cm width and 7.46 sq cm area of the region. The wet thickness of the coating of this adhesive solution is controlled at 500 microns which is then cured in an oven at 60° C. for 10 minutes to form the dried matrix of peripheral region of about 200 microns thick. The peripheral region obtained by this product is designated Intermediate Product A (IP-A).

Ceraphil 31 (by Van Dyk/New Jersey), n-decyl alcohol, dimethyl sulfoxide and ethanol are mixed thoroughly at the weight ratio of 1:1:1:2 to form a homogeneous alcoholic enhancer system (AES). Dissolve excess of LNG in AES to form an oversaturated LNG/AES solution. Carefully dispense 130 microliter of LNG/AES solution by a dispenser onto a piece of 50 micron-thick heat-sealable (ethylene/vinyl acetate) membrane (EVA, 28% vinyl acetate, by 3M Co.) which was precast on the siliconized paper release liner. The dispensed LNG/AES solution is quickly covered with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. The sealing process is performed at 370° F. and 50 psi for 1 (one) second of dwell time. The central region (2.01 sq cm in size) obtained by this process is designated Intermediate Product B (IP-B).

To complete the fabrication of the biregional transdermal drug delivery system, IP-A is carefully laminated on the IP-B by a specially-designed laminating device. The final dosage unit (10 sq cm in size) is cut out by a die cutter.

The novel design of this patch product will allow the two drugs to be delivered simultaneously from a single transdermal dosage unit. LNG is delivered from the central region, while E2 is delivered from the peripheral region. In addition to variation of the formulation ingredients in each region, the daily delivery rate of each drug can be altered by varying the relative size of the surface area of the two regions. This final product has the 2.01 and 7.46 sq cm of surface area for the central and peripheral regions, respectively, to allow desired amount of LNG and E2, respectively, to be delivered. In the in-vitro skin permeation study, this final dosage unit is found to give permeation rates of 3.18 and 0.28 mcg/sq cm/hr of LNG and E2, respectively, which can be translated into the daily delivery rate of 153.3 mcg of LNG and 50.1 mcg of E2.

EXAMPLE 5

A bi-regional transdermal drug delivery system which can simultaneously deliver a progestin, such as levonorgestrel (LNG), and an estrogen, such as 17-beta-estradiol (E2), from its central and peripheral region, respectively, is fabricated by using the following processes and equipment:

Thoroughly mix 0.48 part of E2, 9.68 parts of oleic acid (OA) and 89.64 parts of polyacrylate adhesive solution (Duro-Tak 80-1054, by National Starch and Chemical Co., New Jersey, which contains 36% of solid) by their weight in a container to form a homogeneous E2/OA adhesive solution. This solution is coated onto a silicone-coated release liner (Akrosil B2M) by a specially-designed pattern coating device to form a circular ring of peripheral region. This peripheral region has an inner and outer radius of 0.9 cm and 1.78 cm, respectively, which gives a region having a 0.88 cm width and a 7.46 sq cm area. The wet thickness of the coating of this adhesive solution is controlled at 500 microns which is then cured in an oven at 60° C. for 10 minutes to form the dried matrix of peripheral region about 200 microns thick. The peripheral region obtained by this product is designated Intermediate Product A (IP-A).

Ceraphil 31 (by Van Dyk/New Jersey), n-decyl alcohol, ethyl lactate and propylene glycol are mixed thoroughly at the weight ratio of 1:1:1:2 to form a homogeneous nonethanolic enhancer solvent system (NES). Dissolve excess of LNG in NES to form an oversaturated LNG/NES solution. Carefully dispense 150 microliter of LNG/NES solution by a dispenser onto a piece of 50 micron-thick heat-sealable (ethylene/vinyl acetate) membrane (EVA, 28% vinyl acetate, by 3M Co.) which was precast on the siliconized paper release liner. Quickly cover the dispensed LNG/NES solution with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. Sealing process was performed at 370° F. and 50 psi for 1 (one) second of dwell time. The central region (2.01 sq cm in size) obtained by this process is designated Intermediate Product B (IP-B).

To complete the fabrication of the biregional transdermal drug delivery system, IP-A is carefully laminated on the IP-B by a laminating device. The final dosage unit (10 sq cm in size), is cut out by a die cutter.

The novel design of this patch product allows the two drugs to be delivered simultaneously from a single transdermal dosage unit. LNG is delivered from the central region, while E2 is delivered from the peripheral region. In addition to variation of the formulation ingredients in each region, the daily delivery rate of each drug can be altered by changing the relative size of the surface area of the two regions. This final dosage unit product has the 2.01 and 7.46 sq cm of surface area for the central and peripheral regions, respectively, to allow desired amount of LNG and E2, respectively, to be delivered. In the in-vitro skin permeation study, this final dosage unit is found to give permeation rate of 2.32 and 0.28 mcg/sq cm/hr of LNG and E2, respectively, which can be translated into the daily delivery rate of 112.0 mcg of LNG and 50.1 mcg of E2.

EXAMPLE 6

A bi-regional transdermal drug delivery system which can simultaneously deliver a progestin, such as norethindrone (NET), and an estrogen, such as ethinyl estradiol (EE), from its central and peripheral regions, respectively, can be fabricated by using the following processes and equipment:

Thoroughly mix 0.65 part of EE, 8.96 parts of n-decyl alcohol (n-DA) and 90.39 parts of polyacrylate adhesive solution (Duro-Tak 80-1054, by National Starch and Chemical Co., New Jersey, which contains 36% of solid) by weight in a container to form a homogeneous EE/n-DA adhesive solution. This solution is coated onto a silicone-coated release liner (Akrosil B2M) by a specially-designed pattern coating device to form a circular ring of peripheral region. This peripheral region has an inner and outer radia of 1.956 cm and 2.52 cm, respectively, which gives 0.66 cm to the width and 7.93 sq cm to the area of the region. The wet thickness of the coating of this adhesive solution is controlled at 500 microns which is then cured in an oven at 60° C. for 10 minutes to form the dried matrix of peripheral region about 200 microns thick. The peripheral region obtained by this product is designated Intermediate Product A (IP-A).

Ceraphil 31 (by Van Dyk/New Jersey), n-decyl alcohol, ethyl lactate and propylene glycol are mixed thoroughly at the weight ratio of 1:1:1:2 to form a homogeneous nonethanolic enhancer system (NES). Dissolve excess of LNG in NES to form an oversaturated NET/NES solution. Carefully apply 150 microliter of NET/NES solution by a dispenser onto a piece of 50 micron-thick heat-sealable (ethylene/vinyl acetate) membrane (EVA, 28% vinyl acetate, by 3M Co.), which was precast on a siliconized paper release liner. Quickly cover the dispensed NET/NES solution with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. Sealing process was performed at 370° F. and 50 psi for 1 (one) second of dwell time. The central region (12.0 sq cm in size) obtained by this process is designated Intermediate Product B (IP-B).

To complete the fabrication of the biregional transdermal drug delivery system, IP-A is carefully laminated onto the IP-B by a laminating device. The final product (20 sq cm in size), which is in the form of a transdermal patch, is cut out by a die cutter.

The novel design of this patch product will allow the two drugs to be delivered simultaneously from a single dosage unit. NET is delivered from the central region which does not contain ethanol as solvent, while EE is delivered from the peripheral region. In addition to changing the formulation ingredients in each region, the daily delivery rate of each drug can be altered by varying the relative size of the surface area of the two regions. This final product has 12.0 and 7.93 sq cm of surface area for the central and peripheral regions, respectively, to allow desired amount of NET and EE, respectively, to be delivered. In the in-vitro skin permeation study, this final product was found to give permeation rate of 2.69 and 0.19 mcg/sq cm/hr of NET and EE, respectively, which can be translated into the daily delivery rate of 774.7 mcg of NET and 36.2 mcg of EE.

EXAMPLE 7

A bi-regional transdermal drug delivery system which can simultaneously deliver a progestin, such as medroxy progesterone acetate (MPA), and an estrogen, such as 17-beta-estradiol (E2), from its central and peripheral region, respectively, can be fabricated by using the following processes and equipment:

Thoroughly mix 0.48 part of E2, 9.68 parts of isopropyl myristate (IPM) and 89.84 parts of polyacrylate adhesive solution (Duro-Tak 80-1054, by National Starch and Chemical Co., New Jersey, which contains 36% of solid) by their weight in a container to form a homogeneous E2/IPM adhesive solution. This polyacrylate adhesive has about 5 percent vinyl acetate polymer unit content. This solution is coated onto a silicone-coated release liner (Akrosil B2M) by a specially-designed pattern coating device to form a circular ring of peripheral region. This peripheral region has an inner and outer radia of 2.36 cm and 2.82 cm, respectively, which gives 0.46 cm to the width and 7.50 sq cm to the area of the region. The wet thickness of the coating of this adhesive solution is controlled at 500 microns which is then cured in an oven at 60° C. for 10 minutes to form the dried matrix of peripheral region about 200 microns thick. The peripheral region obtained by this product is designated Intermediate Product A (IP-A).

Ceraphil 31 (by Van Dyk/New Jersey), n-decyl alcohol, ethyl lactate and ethanol are mixed thoroughly at the weight ratio of 1:1:1:2 to form a homogeneous alcoholic enhancer system (AES). Dissolve excess of MPA in AES to form an oversaturated MPA/AES solution. Carefully dispense 150 microliter of MPA/AES solution by a dispenser onto a piece of 50 micron-thick heat-sealable (ethylene/vinyl acetate) membrane (EVA, 28% vinyl acetate, by 3M Co.) which was precast on the siliconized paper release liner. Quickly cover the dispensed MPA/AES solution with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. Sealing process was performed at 370° F. and 50 psi for 1 (one) second of dwell time. The central region (16.0 sq cm in size) obtained by this process is designated Intermediate Product B (IP-B).

To complete the fabrication of the biregional transdermal drug delivery system, IP-A is carefully laminated onto the IP-B by a laminating device. The final product (25.0 sq cm in size), which is in the form of a transdermal patch, can be cut out by a die cutter.

The novel design of this patch product will allow the two drugs to be delivered simultaneously from a single dosage unit. MPA is delivered from the central region, while E2 is delivered from the peripheral region. In addition to variation of the formulation ingredients in each region, the daily delivery rate of each drug can be altered by changing the relative size of the surface area of the two regions. This final product has the 16.0 and 7.50 sq cm of surface area for the central and peripheral regions, respectively, to allow desired amount of MPA and E2, respectively, to be delivered. In the in-vitro skin permeation study, this final product was found to give permeation rate of 39.13 and 0.31 mcg/sq cm/hr of MPA and E2, respectively, which can be translated into the daily delivery rate of 15.03 mcg of MPA and 55.8 mcg of E2.

EXAMPLE 8

A bi-regional transdermal drug delivery system which can simultaneously deliver two androgens, such as testosterone (T) and 17-alpha-methyl testosterone (m-T) and an estrogen, such as 17-beta-estradiol (E2), from its central and peripheral region, respectively, is fabricated by using the following processes and equipment:

Thoroughly mix 0.65 part of E2, 8.96 parts of n-decyl alcohol (n-DA) and 90.39 parts of polyacrylate adhesive solution (Duro-Tak 80-1054, by National Starch and Chemical Co., New Jersey, which contains 36% of solid) by their weight in a container to form a homogeneous E2/n-DA adhesive solution. This solution is coated onto a silicone-coated release liner (Akrosil B2M) by a specially-designed pattern coating device to form a circular ring of peripheral region. This peripheral region has an inner and outer radia of 1.96 cm and 2.52 cm, respectively, which gives 0.56 cm to the width and 7.93 sq cm to the area of the region. The wet thickness of the coating of this adhesive solution is controlled at 500 microns which is then cured in an oven at 60° C. for 10 minutes to form the dried matrix of peripheral region about 200 microns thick. The peripheral region obtained by this product is designated Intermediate Product A (IP-A).

Ceraphil 31 (by Van Dyk/New Jersey), n-decyl alcohol, ethyl lactate and propylene glycol are mixed thoroughly at the weight ratio of 1:1:1:2 to form a homogeneous nonethanolic enhancer system (NES). Dissolve excess amounts of T and m-T in NSS to form an oversaturated T and m-T/NES solution. Carefully dispense 150 microliter of T and m-T/NES solution by a dispenser onto a piece of 50 micron-thick heat-sealable (ethylene/vinyl acetate) membrane (EVA, 28% vinyl acetate, by 3M Co.) which was precast on the siliconized paper release liner. Quickly cover the dispensed T and m-T/NES solution with a piece of drug-impermeable/heat-sealable backing film (Scotch Pak 1109 by 3M Co.). The central region of this biregional drug delivery system is then formed by thermally sealing the backing film to the EVA film by a specially-designed heat seal machine. Sealing process was performed at 370° F. and 50 psi for 1 (one) second of dwell time. The central region (12.0 sq cm in size) obtained by this process is designated Intermediate Product B (IP-B).

To complete the fabrication of the biregional transdermal drug delivery system, IP-A is carefully laminated onto the IP-B by a laminating device. The final product (20 sq cm in size), which is in the form of a transdermal patch, is cut out by a die cutter.

The novel design of this patch product will allow the two drugs to be delivered simultaneously from a single dosage unit of transdermal patch. T and m-T are delivered from the central region, while E2 is delivered from the peripheral region. In addition to changing the formulation ingredients in each region, the daily delivery rate of each drug can be altered by modifying the relative size of the surface area of the two regions. This final product has 12.0 and 7.93 sq cm of surface area for the central and peripheral regions, respectively, to allow desired amount of T, m-T and E2, respectively, to be delivered. In the in-vitro skin permeation study, this final dosage unit is found to give permeation rates of 14.34, 13.64 and 0.24 mcg/sq cm/hr of T, m-T and E2, respectively, which can be translated into the daily delivery rate of 4,130.0 mcg of T, 3,928.3 mcg of m-T and 45.7 mcg of E2.

EXAMPLE 9

A bi-regional transdermal drug delivery system which can simultaneously deliver a progestin, such as progesterone (P4), and an estrogen, such as 17-beta-estradiol (E2), from its central and peripheral regions, respectively, can be fabricated by using the following processes and equipment:

Thoroughly mix 0.48 part of E2, 9.68 parts of isopropyl myristate (IPM) and 89.84 parts of polyacrylate adhesive solution (Duro-Tak 80-1054, by National Starch and Chemical Co., New Jersey, which contains 36% of solid) by weight in a container to form a homogeneous E2/IPM adhesive solution. This solution is coated onto a silicone-coated release liner (Akrosil B2M) by a specially-designed pattern coating device to form a circular ring of peripheral region. This peripheral region has an inner and outer radia of 2.36 cm and 2.82 cm, respectively, which gives a region having 0.46 cm width and 7.50 sq cm area. The wet thickness of the coating of this adhesive solution is controlled at 500 microns which is then cured in an oven at 60° C. for 10 minutes to form the dried matrix of peripheral region having a thickness of about 200 microns. The peripheral region obtained by this product is designated Intermediate Product A (IP-A).

Ceraphil 31 (by Van Dyk/New Jersey), n-decyl alcohol, ethyl lactate and ethanol are mixed thoroughly at the weight ratio of 1:1:1:2 to form a homogeneous alcoholic enhancer system (AES). Dissolve excess amount of P4 in AES to form an oversaturated P4/AES solution. Carefully dispense 150 microliter of P4/AES solution by a dispenser onto a piece of 50 micron-thick heat-sealable (ethylene/vinyl acetate) membrane (EVA, 28% vinyl acetate, by 3M Co.) which was precast on the siliconized paper release liner. Quickly cover the dispensed P4/AES solution with a piece of drug-impermeable/heat-sealable backing film (Scotch Pak 1109 by 3M Co.). The central region of this biregional drug delivery system is then formed by thermally sealing the backing film to the EVA film by a specially designed heat seal machine. Sealing process was performed at 370° F. and 50 psi for 1 (one) second of dwell time. The central region (16.0 sq cm in size) obtained by this process is designated Intermediate Product B (IP-B).

To complete the fabrication of the biregional transdermal drug delivery system, IP-A is carefully laminated onto the IP-B by a laminating device. The final dosage unit product (25.0 sq cm in size), is cut out by a die cutter.

The novel design of this dosage unit product allows the two drugs to be delivered simultaneously. P4 is delivered from the central region, while E2 is delivered from the peripheral region. In addition to variation of the formulation ingredients in each region, the daily delivery rate of each drug can be altered by changing the relative size of the surface area of the two regions. This dosage unit has the 16.0 and 7.50 sq cm of surface area for the central and peripheral regions, respectively, to allow desired amount of P4 and E2, respectively, to be delivered. In the in-vitro skin permeation study, this final product was found to give permeation rate of 44.88 and 0.31 mcg/sq cm/hr of P4 and E2, respectively, which can be translated into the daily delivery rate of 17.23 milligram of P4 and 55.8 mcg of E2.

EXAMPLE 10

This example describes multi-region transdermal contraceptive delivery (mr-TCD) dosage units and methods for making them. The dosage units can be designed to deliver different contraceptive steroid hormones from different regions within a single dosage unit. Combination of a progestin and an estrogen can be delivered transdermally from a single dosage unit of this system to achieve desired contraceptive efficacy. The dosage unit has a hormone-containing layer having different regions in which different steroids with/without skin permeation enhancers are contained. A region can contain a progestin with enhancer(s) while another region can contain an estrogen without enhancer(s) or with different enhancer(s). If desired, a mr-TCD system can have a region which contains no steroid hormones and no skin permeation enhancer and which is used to segregate the other hormone-containing regions. The location and the area of each region in a mr-TCD system cay vary and can be specifically designed to control the release of hormones at optimal rates to achieve greater contraceptive efficacy.

Factors that can be varied to control the amount or ratio of amount of progestin and estrogen from such a system include:

1. Area and area ratio of each region.
2. Hormone concentration in the polymer or polymer adhesive which forms each region.
3. Types of polymer or polymer adhesive which form each region.
4. Types of skin permeation enhancers incorporated in the polymer or polymer adhesive.
5. Amount of skin permeation enhancer(s) incorporated in the polymer or polymer adhesive.
6. Thickness of coating of each region.

Figure 18A:
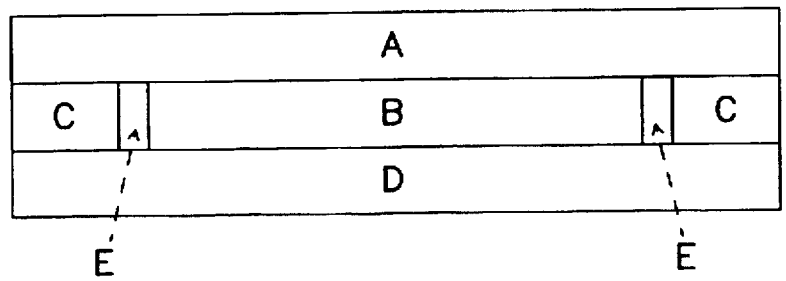
FIG. 18 shows a dosage unit wherein two distinct reservoirs are present, the reservoirs having pharmaceuticals A and B, respectively. The reservoirs have the pharmaceuticals present in a matrix form.
Figure 18B:
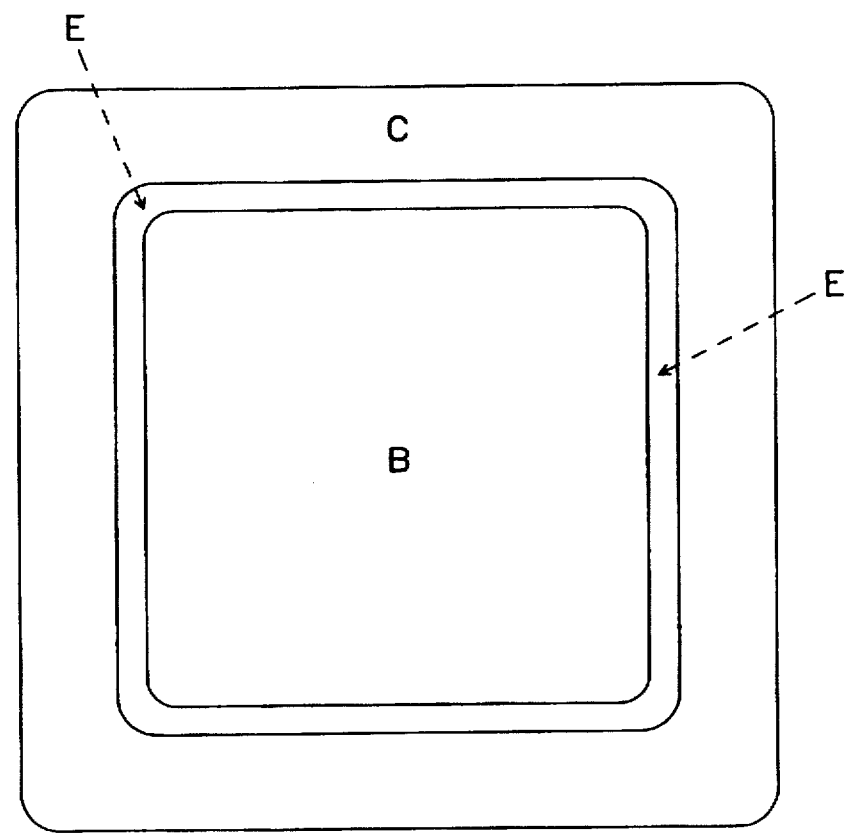

FIG. 18 shows a cross sectional view of a dosage unit and top plan view of a three-region mr-TCD system. This system consists of the following elements:

A. Low adhesion hormone-impermeable release liner.

B. Central-region, which contains hormone with/without skin permeation enhancers.

C. Peripheral-region, which contains hormone with/without skin permeation enhancers.

D. Hormone-impermeable backing layer.

E. Barrier region which contains no hormones nor skin permeation enhancers.

The selection of which hormone (estrogen or progestin) to incorporate into which region (either central or peripheral) depends on therapeutic needs, formulation factors and fabrication procedures.

If skin permeation enhancer is incorporated in the central region B along with a progestin, an estrogen can be incorporated in peripheral region C which contains no or very little skin permeation enhancer. By such a configuration, the estrogen-containing peripheral region C can also serve as a peripheral adhesive ring which will help to maintain adhesiveness of the whole mr-TCD on the application site of the skin. This configuration is especially useful in the situation in which the central region B is required to contain higher concentration of skin permeation enhancer in order to achieve desired skin permeation rate of progestin and thereby loses adequate adhesiveness. Therefore, as a general rule, the region which contains formulation that is more adhesive to the skin should be assigned as peripheral region.

The estrogens that can be used in this system include 17-estradiol, ethinyl estradiol, and others described above. Progestins, such as levonorgestrel, norethindrone, and others described above, can be used with the estrogen used. Skin permeation enhancers of various types as described above, surfactants (anionic, cationic, non-ionic and zwitterionic types), and the combination of surfactants with straight long-chain alkanols, alkanoic acids or alkanoic acid esters, can be used in various concentrations in the central region of the mr-TCD system. Region E can be left as a trench or be filled with a material, such as a polymer or polymer adhesive, to prevent or to inhibit the inter-regional migration of hormones and/or skin permeation enhancers. The polymers used to construct this band can be selected from high-density polyethylene, polypropylene, polystyrene, polyisobutylene, and other suitable materials.

On a piece of backing laminate (Scotch Pak 1109, 3M Co.), a layer of adhesive solution (Duro-Tak 80-1054, National Starch and Chemical Co.) is applied at the thickness of 200 microns. This adhesive solution contains 1% (W/W) estradiol (E2) and 10% (W/W) of n-decyl alcohol (n-DA). The coating of this E2/n-DA adhesive solution is applied to form the peripheral region C as shown in FIG. 18. Coating is performed by using a sophisticated Laboratory Coater (Type LTSV, Werner Mathis AG) which is equipped with specially-designed coating head and micrometers to control the thickness of coating. The peripheral coating C is then dried at 60° C. for 10 minutes using Laboratory Dryer (Type LTF, Werner Mathis AG). This peripheral coating is hereafter called intermediate product (I). Using the same equipment, a layer of 20% (W/W) polyisobutylene (Oppanol B80, BASF Co.) solution is coated onto the low-adhesion side of release liner (Scotch Pak 1022, 3M Co.) at the thickness of 600 microns. This coating is dried at 50° C. for 5 minutes using the same drier used in the previous step. The dried coating of polyisobutylene polymer band is then laminated to the intermediate product (I) and then the release liner is removed to form the region D as shown in FIG. 18. The product obtained is thereafter called intermediate product (II). Again, using the same coating equipment, a layer of Duro-Tak (80-1054, National Starch and Chemical Co.) adhesive solution containing 1% (W/W) of levonorgestrel, 10% of Span 20 (Sigma Chemical Co.), 10% propylene glycol (Fisher Scientific Co.) and 10% of lauric acid (Sigma Chemical Co.) are coated onto the intermediate product (II) at the thickness of 400 microns. The coating is dried at 60° C. for 15 minutes in the same drier used in the previous steps. After the drying is complete, the coating of the three regions is then covered with a release liner (Scotch Pak 1022, 3M Co.). The product obtained after this step of coating, drying and lamination processes consists of three concentric regions as shown in FIG. 18. The area ratio of region C over region B, in this case, is 1.25:1. The long-term (140 hours) in-vitro skin permeation rates of levonorgestrel and estradiol were found to be 0.52 (±0.07) and 0.20 (±0.03) mcg/sq cm/hr, respectively, when adult Caucasian female cadaver skin was used in the in-vitro test procedure. If the area of region B is 5 sq cm (are of region C becomes 6.25 sq cm) a mr-TCD system of this configuration and size would be able to simultaneously deliver 62.4 (±8.4) mcg of levonorgestrel and 30.0 (±4.5) mcg of estradiol per day. Therefore, ratio of daily delivery rate of levonorgestrel/estradiol is calculated as 2.08.

This example illustrates that by controlling the composition of enhancers, drug loading, thickness of coating area of each region, the ratio of daily delivery rate of progestin/estrogen can be controlled by using the mr-TCD system described above.

The shape of the dosage units can be varied. The regions can be parallel strips or have other appropriate shapes and/or configurations.

Ethinyl estradiol or other estrogens can be used and the progestins described above can be used instead of 17-beta-estradiol and levonorgestrel, respectively.

What is claimed is:

1. A transdermal dosage unit comprising:
   a. a backing layer which is impervious to the ingredients of the dosage unit; and
   b. a reservoir layer having a reservoir compartment region and an outer wall, said reservoir compartment region containing a liquid medium in which one or more pharmaceuticals are dissolved, and said outer wall being a permeability-regulating polymer membrane which is an (ethylene/vinyl acetate) copolymer having a vinyl acetate content of about 18 to about 40 percent by mean weight of the copolymer wherein the polymer membrane is non-porous;

wherein said dosage unit provides an absorption rate of said one or more pharmaceuticals that is essentially constant for at least 24 hours and provides effective amounts of said one or more pharmaceuticals through transdermal absorption, and wherein said dosage unit is adapted to adhere to the skin of a subject using said dosage unit, and wherein said pharmaceuticals are selected from the group consisting of levonorgestrel, 17-beta estradiol, norethindione, ethyl estradiol, medroxy progesterone acetate, and testosterone.

2. A dosage unit of claim 1 wherein the reservoir layer has an adhesive region which is separate from said reservoir compartment region.

3. A dosage unit of claim 1 wherein the outer wall has applied thereto an adhesive layer adapted to adhere said dosage unit to said subject.

4. A dosage unit of claim 1 wherein said liquid medium is a biocompatible combination of at least two miscible solvents.

5. A dosage unit of claim 4 wherein one of said at least two miscible solvents is water.

6. A dosage unit of claim 4 wherein the combination of miscible solvents comprise water and ethyl alcohol.

7. A dosage unit of claim 1 wherein said liquid medium comprises a $C_3$–$C_4$ alkane diol.

8. A dosage unit of claim 1 wherein the solvent is propylene glycol.

9. A dosage unit of claim 1 wherein said pharmaceuticals is 17-beta-estradiol.

10. A dosage unit of claim 1 wherein said dosage unit has an effective amount of one or more transdermal absorption enhancers.

11. A dosage unit of claim 10 wherein said transdermal absorption enhancer is selected from the group consisting of long chain alkanoic acids, long chain alkanols, alkyl esters of lactic acids and combinations thereof.

* * * * *

UNITED STATES PATENT AND TRADEMARK OFFICE
CERTIFICATE OF CORRECTION

PATENT NO. : 5,788,983
DATED : August 4, 1999
INVENTOR(S) : Yie W. Chien, et. al.

It is certified that error appears in the above-identified patent and that said Letters Patent is hereby corrected as shown below:

Title page, item [63], delete "Ser. No. 332,471, Apr. 3, 1989, abandoned" and insert --Ser. No. 07/332,471, Pat. No. 5,296,230, issued Mar. 22,1994--, Column 1, line 8, delete "U.S. application Ser. No. 07/332,471, filed Apr. 3, 1989 now abandoned." and insert --Ser. No. 07/332,471, now U.S. Pat. 5,296,230, issued Mar. 22, 1994--.

Signed and Sealed this

Second Day of May, 2000

Attest:

Q. TODD DICKINSON

*Attesting Officer*  *Director of Patents and Trademarks*